(12) United States Patent
Tsusaka et al.

(10) Patent No.: US 9,573,274 B2
(45) Date of Patent: Feb. 21, 2017

(54) APPARATUS FOR FLEXIBLE ELONGATE MEMBER, METHOD FOR FLEXIBLE ELONGATE MEMBER, AND STORAGE MEDIUM

(71) Applicant: Panasonic Intellectual Property Management Co., Ltd., Osaka (JP)

(72) Inventors: Yuko Tsusaka, Osaka (JP); Yudai Fudaba, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 96 days.

(21) Appl. No.: 14/663,264

(22) Filed: Mar. 19, 2015

(65) Prior Publication Data

US 2015/0272684 A1    Oct. 1, 2015

(30) Foreign Application Priority Data

Mar. 31, 2014 (JP) ................................. 2014-073377

(51) Int. Cl.
| | |
|---|---|
| B25J 9/16 | (2006.01) |
| A61B 19/00 | (2006.01) |
| B25J 3/00 | (2006.01) |
| A61B 34/32 | (2016.01) |
| A61M 25/01 | (2006.01) |

(52) U.S. Cl.
CPC .............. *B25J 9/1633* (2013.01); *A61B 34/37* (2016.02); *A61B 34/32* (2016.02); *A61B 34/77* (2016.02); *A61B 2034/301* (2016.02); *A61M 25/0116* (2013.01); *G05B 2219/39322* (2013.01); *G05B 2219/39343* (2013.01)

(58) Field of Classification Search
CPC ......................... A61M 25/09041; B25J 9/1633
See application file for complete search history.

(56) References Cited

U.S. PATENT DOCUMENTS

| | | | |
|---|---|---|---|
| 2009/0247943 A1* | 10/2009 | Kirschenman | A61B 19/2203 604/95.04 |
| 2011/0077681 A1 | 3/2011 | Nagano et al. | |
| 2014/0276389 A1* | 9/2014 | Walker | A61M 25/09041 604/95.01 |

FOREIGN PATENT DOCUMENTS

JP    2009-285150    12/2009

* cited by examiner

*Primary Examiner* — Dale Moyer
(74) *Attorney, Agent, or Firm* — Wenderoth, Lind & Ponack, L.L.P.

(57) ABSTRACT

An insertion method for a flexible elongate member is used to insert the flexible elongate member into a tube while causing first and second holding units to perform an opening-and-closing operation for holding and releasing the flexible elongate member. The method includes acquiring information of a distance by which the second holding unit moves with respect to the first holding unit and information of an operation type used to distinguish between insertion of the flexible elongate member into the tube, stoppage of the flexible elongate member, and extraction of the flexible elongate member from the tube; generating operation information regarding an opened/closed state of the first holding portion and an opened/closed state of the second holding portion on the basis of the distance and the operation type; and controlling the insertion, stoppage, or extraction of the flexible elongate member on the basis of the operation information.

14 Claims, 30 Drawing Sheets

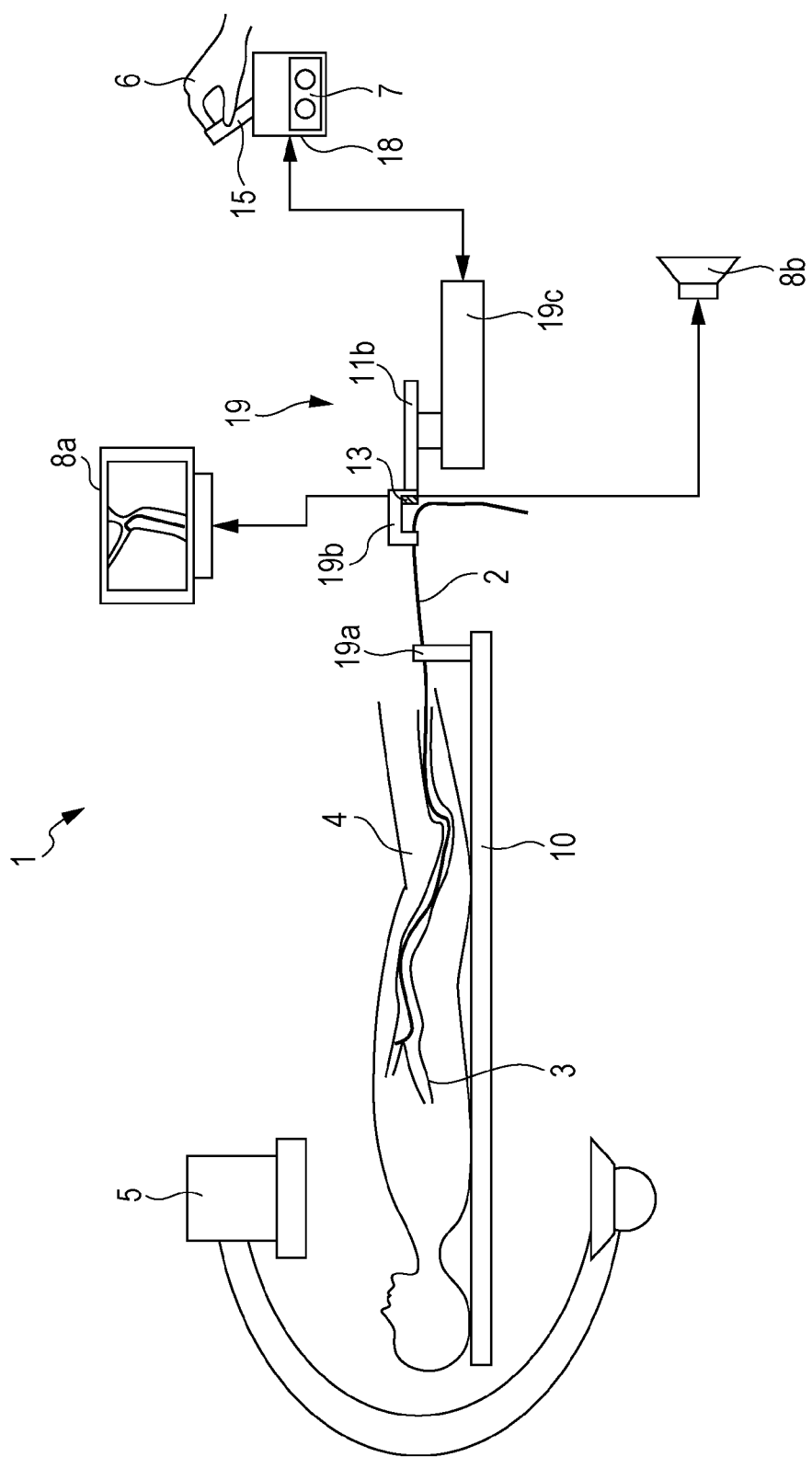

FIG. 7

| TIME (msec) | OPERATION TYPE | MASTER MOVEMENT AMOUNT (m) | POSITION OF SLAVE INSERTION UNIT (m) | FIRST OPENING-AND-CLOSING PORTION | SECOND OPENING-AND-CLOSING PORTION | FORCE (N, Nm) |
|---|---|---|---|---|---|---|
| t0 | 1 | pm0 | lm0 | 0 | 1 | fs0 |
| t1 | 1 | 0 | lm1 | 1 | 0 | fs1 |
| t2 | 2 | 0 | lm2 | 1 | 0 | fs2 |
| t3 | 2 | pm1 | lm3 | 0 | 1 | fs3 |
| t4 | 0 | 0 | lm3 | 1 | 1 | fs4 |
| ..... | ..... | ..... | ..... | ..... | ..... | ..... |

| LEVER ANGLE | SPEED |
|---|---|
| r0 | v0 |
| r1 | v1 |
| .. | .. |
| r5=0 | v5=0 |
| r6 | v6 |
| ⋮ | ⋮ |
| r11 | v11 |

FIG. 14

| TIME (msec) | OPERATION TYPE | MASTER MOVEMENT AMOUNT (m) | POSITION OF SLAVE INSERTION UNIT (m) | FIRST OPENING-AND-CLOSING PORTION | SECOND OPENING-AND-CLOSING PORTION | FORCE (N, Nm) |
|---|---|---|---|---|---|---|
| t0 | 1 | pm0 | lm0 | 0 | 1 | fs0 |
| t1 | 1 | 0 | lm0 | 1 | 1 | fs1 |
| t2 | 1 | 0 | lm1 | 1 | 0 | fs2 |
| t3 | 2 | 0 | lm2 | 1 | 0 | fs3 |
| t4 | 2 | 0 | lm2 | 1 | 1 | fs4 |
| t5 | 2 | pm1 | lm3 | 0 | 1 | fs5 |
| . . . . | . . . . | . . . . | . . . . | . . . . | . . . . | . . . . |

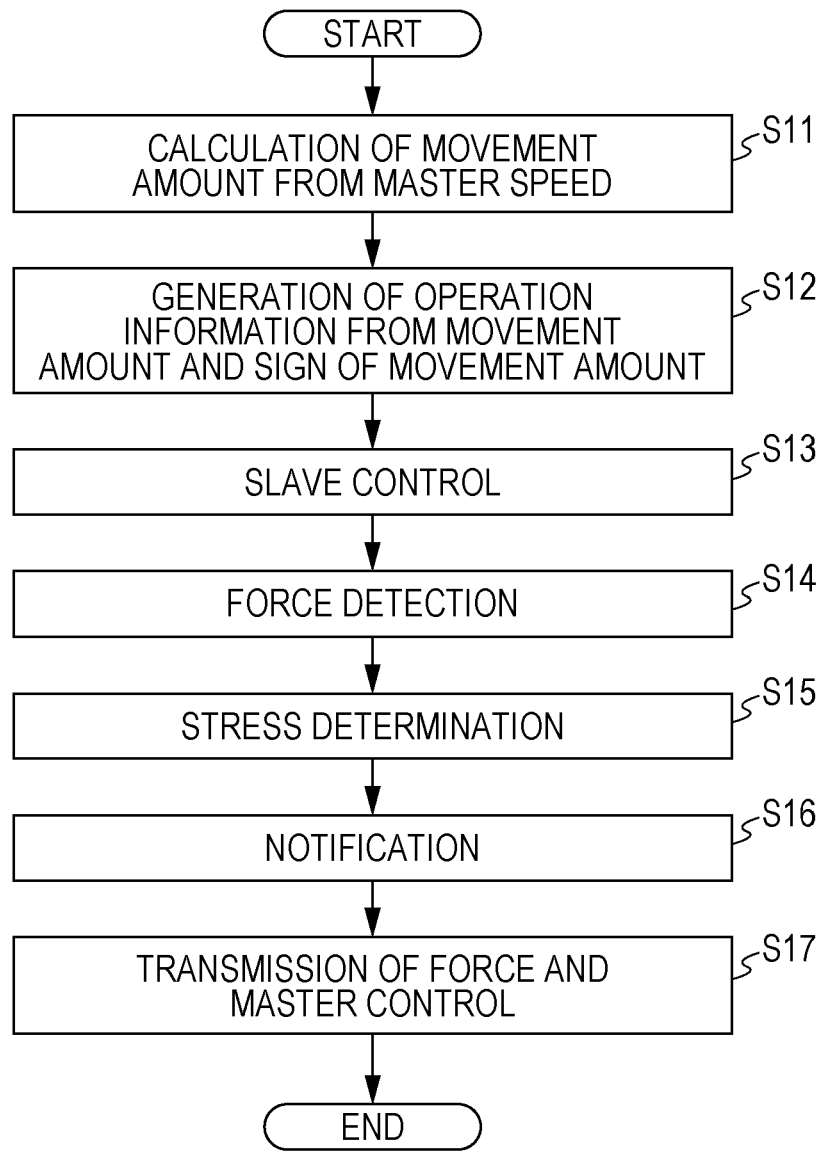

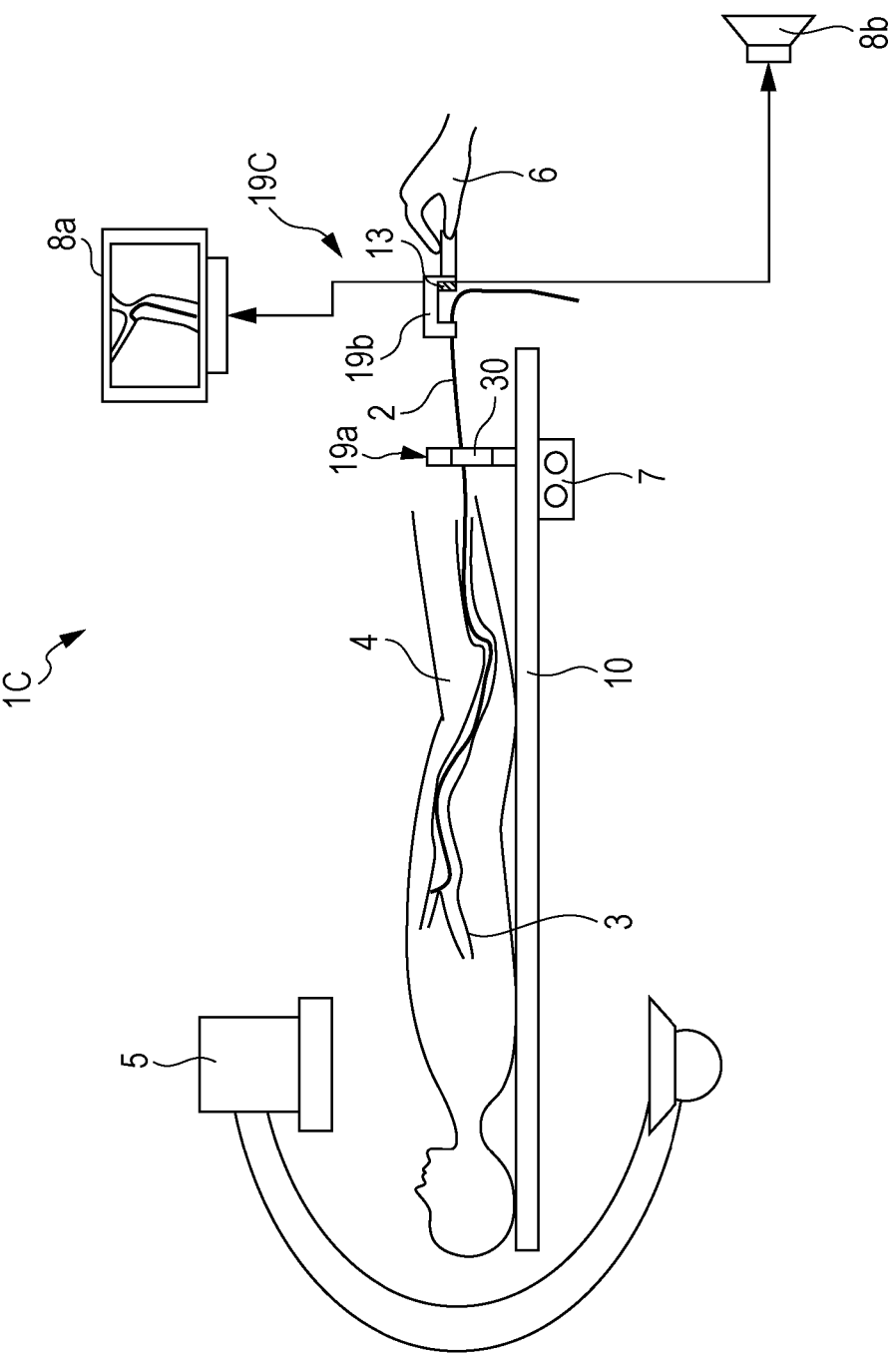

FIG. 21

| TIME (msec) | OPERATION TYPE | DISTANCE (m) | FIRST OPENING-AND-CLOSING PORTION | SECOND OPENING-AND-CLOSING PORTION | FORCE (N, Nm) |
|---|---|---|---|---|---|
| t0 | 1 | lm0 | 0 | 1 | fs0 |
| t1 | 1 | lm1 | 1 | 0 | fs1 |
| t2 | 2 | lm2 | 1 | 0 | fs2 |
| t3 | 2 | lm3 | 0 | 1 | fs3 |
| t4 | 0 | lm3 | 1 | 1 | fs4 |
| ⋮ | ⋮ | ⋮ | ⋮ | ⋮ | ⋮ |

| DISTANCE THRESHOLD (m) |
|---|
| L1 = Le1 |
| L2 = Le2 |

APPARATUS FOR FLEXIBLE ELONGATE MEMBER, METHOD FOR FLEXIBLE ELONGATE MEMBER, AND STORAGE MEDIUM

BACKGROUND

1. Technical Field

The present disclosure relates to an apparatus for a flexible elongate member, a method for a flexible elongate member, and a storage medium, which are used to assist an operation of, for example, inserting a flexible elongate member into a tube.

2. Description of the Related Art

In recent years, an operation method of inserting a flexible elongate member, such as a guidewire or a catheter, into a tube of a human body, such as a blood vessel, while observing a fluoroscopic image or the like has been used, for example, to treat angiostenosis. This operation method is generally carried out while an operator observes an image of the tube or the flexible elongate member to check the state of the tube or the flexible elongate member and, at the same time, directly senses a force related to insertion resistance, which is generated when the flexible elongate member comes into contact with the tube, with their hand.

In a manufacturing site, an operation of assembling a flexible elongate member like an optical fiber, or inserting a flexible elongate member like a wire or a hose into a pipe, is performed. A worker performs such an operation while directly sensing a force with their hand to prevent damage to the optical fiber or the pipe.

In any of the above-described operations, the force related to the insertion resistance applied to the flexible elongate member can only be recognized by the operator or worker, and cannot be quantified into numerical values or the like. Also, it is difficult to appropriately insert the flexible elongate member up to a desired position due to the insertion resistance applied to the flexible elongate member.

To solve the above-described problems, Japanese Unexamined Patent Application Publication No. 2009-285150 proposes a method for inserting the flexible elongate member by using a coil insertion apparatus while measuring, from the outside of the human body, the insertion resistance force applied to the flexible elongate member. The insertion resistance is measured by measuring the degree of bending of the flexible elongate member. With this method, the insertion resistance force applied to the flexible elongate member can be measured quantitatively, and the flexible elongate member can be inserted by using the insertion apparatus.

With the method according to Japanese Unexamined Patent Application Publication No. 2009-285150, no sensor is directly provided on the insertion apparatus or the flexible elongate member, and the force related to the insertion resistance applied to the flexible elongate member can be measured from the outside of the human body. However, this method is not convenient because the degree of bending of the flexible elongate member is detected by an optical sensor and the manner in which the flexible elongate member is bent varies depending on the rigidity of the flexible elongate member. In particular, when the flexible elongate member is made of a plurality of materials, the relationship between the degree of bending and the force needs to be determined experimentally. In addition, the detection accuracy of the method according to Japanese Unexamined Patent Application Publication No. 2009-285150, in which the force is estimated by measuring a current of a motor that drives a roller, is lower than that of a measurement method in which a known strain gauge or the like is used.

SUMMARY

One non-limiting and exemplary embodiment provides an apparatus for a flexible elongate member, the apparatus being capable of measuring a force by using a known strain gauge or the like.

In one general aspect, the techniques disclosed here feature apparatus for a flexible elongate member including a first holding unit that is capable of holding the flexible elongate member by closing a first opening-and-closing portion and that is capable of releasing the flexible elongate member by opening the first opening-and-closing portion; a second holding unit that is capable of moving with respect to the first holding unit, that performs an opening-and-closing operation independently of an opening-and-closing operation of the first holding unit, that is capable of holding the flexible elongate member by closing a second opening-and-closing portion, and that is capable of releasing the flexible elongate member by opening the second opening-and-closing portion; an information acquiring unit that acquires information of a distance of the second holding unit with respect to the first holding unit and information of an operation type including information indicating insertion of the flexible elongate member into a tube, extraction of the flexible elongate member from the tube, or stoppage of the insertion and the extraction; an operation information generator that generates operation information on the basis of the acquired information of the distance and the acquired information of the operation type, the operation information including information indicating whether to open or close the first holding unit and information indicating whether to open or close the second holding unit; and an operation controller that controls the insertion, the extraction, and the stoppage of the insertion and the extraction on the basis of the operation information.

According to the present disclosure, by controlling the operation of the holding units that hold the flexible elongate member, an operation of, for example, inserting the flexible elongate member can be performed while a force is measured with a known strain gauge or the like.

It should be noted that general or specific embodiments may be implemented as a system, a method, an integrated circuit, a computer program, a computer-readable storage medium, or any combination of two or more of an apparatus, a system, a method, an integrated circuit, a computer program, and a computer-readable storage medium. The computer-readable storage medium may be, for example, a non-transitory storage medium such as a compact disc read-only memory (CD-ROM).

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 1 illustrates the outline of the structure of an insertion apparatus according to a first embodiment of the present disclosure and the manner in which the insertion apparatus is used;

FIG. 7 illustrates an operation information database according to the first embodiment of the present disclosure;

FIG. 14 illustrates an operation information database according to the second embodiment of the present disclosure;

FIG. 16 is a flowchart for the insertion apparatus according to the second embodiment of the present disclosure;

FIG. 17 illustrates the outline of the structure of an insertion apparatus according to a third embodiment of the present disclosure;

FIG. 21 illustrates an operation information database according to the third embodiment of the present disclosure;

DETAILED DESCRIPTION

Figure 2A:
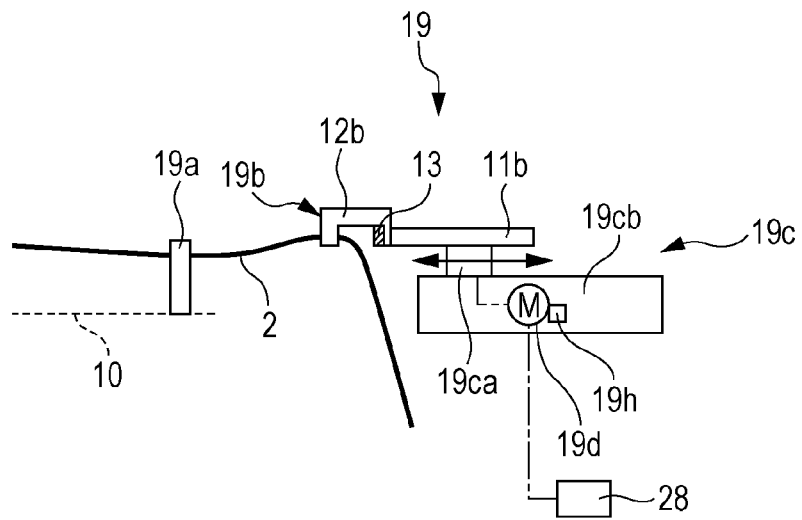
FIG. 2A illustrates the structure of a slave robot according to the first embodiment of the present disclosure.

Embodiments of the present disclosure will be described in detail with reference to the drawings.

Before describing the embodiments of the present disclosure in detail with reference to the drawings, various aspects of the present disclosure will be described.

According to a first aspect of the present disclosure, an apparatus for a flexible elongate member includes a first holding unit that is capable of holding the flexible elongate member by closing a first opening-and-closing portion and that is capable of releasing the flexible elongate member by opening the first opening-and-closing portion; a second holding unit that is capable of moving with respect to the first holding unit, that performs an opening-and-closing operation independently of an opening-and-closing operation of the first holding unit, that is capable of holding the flexible elongate member by closing a second opening-and-closing portion, and that is capable of releasing the flexible elongate member by opening the second opening-and-closing portion; an information acquiring unit that acquires information of a distance of the second holding unit with respect to the first holding unit and information of an operation type including information indicating insertion of the flexible elongate member into a tube, extraction of the flexible elongate member from the tube, or stoppage of the insertion and the extraction; an operation information generator that generates operation information on the basis of the acquired information of the distance and the acquired information of the operation type, the operation information including information indicating whether to open or close the first holding unit and information indicating whether to open or close the second holding unit; and an operation controller that controls the insertion, the extraction, and the stoppage of the insertion and the extraction on the basis of the operation information.

With this structure, by controlling the operation of the holding units that hold the flexible elongate member, an operation of, for example, inserting the flexible elongate member can be performed while a force is measured with a known strain gauge or the like.

According to a second aspect of the present disclosure, in the apparatus according to the first aspect, when the insertion or the extraction is performed, the operation information generator generates, as the operation information, information including information indicating that the first holding unit is to be opened and the second holding unit is to be closed.

With this structure, the flexible elongate member can be inserted into or extracted from the tube by moving the second holding unit that holds the flexible elongate member.

According to a third aspect of the present disclosure, in the apparatus according to the first or second aspect, when the insertion or the extraction is performed and when the second holding unit is moved while the flexible elongate member is held by the first holding unit, the operation information generator generates, as the operation information, information including information indicating that the first holding unit is to be closed and the second holding unit is to be opened.

With this structure, an operation of preparing for the insertion or extraction of the flexible elongate member by the second holding unit can be performed by moving the second holding unit that does not hold the flexible elongate member while the first holding unit is closed to hold the flexible elongate member.

According to a fourth aspect of the present disclosure, in the apparatus according to the first aspect, when the insertion and the extraction is to be stopped, the operation information generator generates, as the operation information, information including information indicating that the first holding unit is to be closed.

With this structure, the insertion of the flexible elongate member by the insertion apparatus can be stopped.

According to a fifth aspect of the present disclosure, in the apparatus according to the first aspect, when the insertion or the extraction is performed, the operation information generator generates, as the operation information, information including information indicating that the first holding unit is to be opened and the second holding unit is to be closed after the first holding unit and the second holding unit are closed at the same time.

With this structure, when the flexible elongate member is inserted or extracted, the flexible elongate member is prevented from being accidentally moved with respect to the tube by closing the first holding unit and the second holding unit at the same time so that the flexible elongate member is held by both the first holding unit and the second holding unit.

According to a sixth aspect of the present disclosure, the apparatus according to the first aspect further includes a master mechanism that acquires the distance as an amount of movement of the flexible elongate member; and an insertion unit that moves the second holding unit linearly by a distance corresponding to the amount of movement by a driving operation of a drive device, and the information of the distance is based on a position of the second holding unit at the insertion unit.

With this structure, by using the master mechanism and the insertion unit mounted in a slave mechanism, the insertion speed may be set to, for example, a constant value by moving the second holding unit linearly by the driving operation of the drive device.

According to a seventh aspect of the present disclosure, in the apparatus according to the first aspect, the information acquiring unit includes a distance detector that detects the distance. When the operation type is the insertion, the operation information generator generates, as the operation information, information including information indicating that the first holding unit is to be opened and the second holding unit is to be closed at the time when the distance detected by the distance detector becomes greater than or equal to a predetermined first threshold, and then the first holding unit is to be closed and the second holding unit is to be opened to release the flexible elongate member at the time when the distance detected by the distance detector becomes smaller than or equal to a predetermined second threshold. When the operation type is the extraction, the operation information generator generates, as the operation information, information including information indicating that the first holding unit is to be closed and the second holding unit is to be opened at the time when the distance detected by the distance detector becomes greater than or equal to the predetermined first threshold, and then the first holding unit is to be opened and the second holding unit is to be closed at the time when the distance detected by the distance detector becomes smaller than or equal to the predetermined second threshold. When the operation type is the stoppage of the insertion and the extraction, the operation information generator generates, as the operation information, information including information indicating that the first holding unit is to be closed.

With this structure, even when the insertion or extraction speed varies, such as when the worker moves the second holding unit manually, the flexible elongate member can be reliably inserted into the tube or extracted from the tube.

According to an eighth aspect of the present disclosure, the apparatus according to any one of the first to seventh aspects further includes a force detector that is provided on the second holding unit and that detects information of a force applied to the flexible elongate member, and a determining unit that determines that stress is placed on the flexible elongate member or the tube when the information of the force detected by the force detector is greater than or equal to a threshold.

With this structure, by inserting the flexible elongate member into the tube while measuring the force with the force detector, whether or not stress is placed on the flexible elongate member or the tube can be determined by the determining unit.

According to a ninth aspect of the present disclosure, the apparatus according to the eighth aspect further includes a first notifying unit that displays a result of the determination performed by the determining unit together with a captured image of the tube or the flexible elongate member.

With this structure, the worker can check the stress placed on the flexible elongate member or the tube based on the display presented by the notifying unit.

According to a tenth aspect of the present disclosure, the apparatus according to the eighth or ninth aspect further includes a second notifying unit that emits a sound to notify a worker of a result of the determination performed by the determining unit.

With this structure, the worker can check the stress placed on the flexible elongate member or the tube based on the sound.

According to an eleventh aspect of the present disclosure, in the apparatus according to any one of the eighth to tenth aspects, when the determining unit determines that stress is placed on the tube or the flexible elongate member, the operation information generator generates, as the operation information, information indicating that the first holding unit is to be closed.

With this structure, the insertion can be stopped when stress is placed on the flexible elongate member or the tube.

According to a twelfth aspect of the present disclosure, the apparatus according to any one of the eighth to eleventh aspects further includes a force transmitting unit that transmits a force to a master mechanism on the basis of the force detected by the force detector, the master mechanism being manipulated by a worker.

With this structure, owing to the force transmitting unit, the worker can perform an operation while sensing a force with their hand.

According to a thirteenth aspect of the present disclosure, a method for a flexible elongate member includes acquiring information of a distance of a second holding unit with respect to a first holding unit and information of an operation type including information indicating insertion of the flexible elongate member into a tube, extraction of the flexible elongate member from the tube, or stoppage of the insertion and the extraction, the first holding unit being capable of holding the flexible elongate member by closing a first opening-and-closing portion and being capable of releasing the flexible elongate member by opening the first opening-and-closing portion, the second holding unit being capable of moving with respect to the first holding unit, performing an opening-and-closing operation independently of an opening-and-closing operation of the first holding unit, being capable of holding the flexible elongate member by closing a second opening-and-closing portion, and being capable of releasing the flexible elongate member by opening the second opening-and-closing portion; generating operation information on the basis of the acquired information of the distance and the acquired information of the operation type, the operation information including information indicating whether to open or close the first holding unit and information indicating whether to open or close the second holding unit; and controlling the insertion, the extraction, and the stoppage of the insertion and the extraction on the basis of the operation information.

With this structure, by controlling the operation of the holding units that hold the flexible elongate member, insertion of the flexible elongate member can be performed while a force is measured with a known strain gauge or the like.

According to a fourteenth aspect of the present disclosure, a non-transitory computer-readable storage medium stores a control program for causing an apparatus including a processor to execute a method for a flexible elongate member, the method comprising acquiring information of a distance of a second holding unit with respect to a first holding unit and information of an operation type including information indicating insertion of the flexible elongate member into a tube, extraction of the flexible elongate member from the tube, or stoppage of the insertion and the extraction, the first holding unit being capable of holding the flexible elongate member by closing a first opening-and-closing portion and being capable of releasing the flexible elongate member by opening the first opening-and-closing portion, the second holding unit being capable of moving with respect to the first holding unit, performing an opening-and-closing operation independently of an opening-and-closing operation of the first holding unit, being capable of holding the flexible elongate member by closing a second opening-and-closing portion, and being capable of releasing the flexible elongate member by opening the second opening-and-closing portion; generating operation information on the basis of the acquired information of the distance and the acquired information of the operation type, the operation information including information indicating whether to open or close the first holding unit and information indicating whether to open or close the second holding unit; and controlling the insertion, the extraction, and the stoppage of the insertion and the extraction on the basis of the operation information.

With this structure, by controlling the operation of the holding units that hold the flexible elongate member, insertion of the flexible elongate member can be performed while a force is measured with a known strain gauge or the like.

According to a fifteenth aspect of the present disclosure, an apparatus for a flexible elongate member includes a first holding unit capable of holding the flexible elongate member; and a second holding unit capable of holding the flexible elongate member. When a first portion of the flexible elongate member is inserted into a tube, the first holding unit holds a second portion of the flexible elongate member without the flexible elongate member being held by the second holding unit, and then the second holding unit holds a third portion of the flexible elongate member without the flexible elongate member being held by the first holding unit. A distance between first portion and the third portion of the flexible elongate member is less than a distance between the first portion and the second portion of the flexible elongate member.

Embodiments of the present disclosure will now be described with reference to the drawings.

First Embodiment

First, the outline of an insertion apparatus 1 for a flexible elongate member according to a first embodiment of the present disclosure will be described.

FIG. 1 illustrates a catheter test or treatment in which an operator 6, an example of a worker, inserts a guidewire 2, which is an example of a flexible elongate member, into a human body 4 from the outside. The guidewire 2 is inserted toward an affected part of a blood vessel 3, which is an example of a tube, of a brain or heart of the human body 4. The human body 4 lies on a table 10.

Figure 2B:
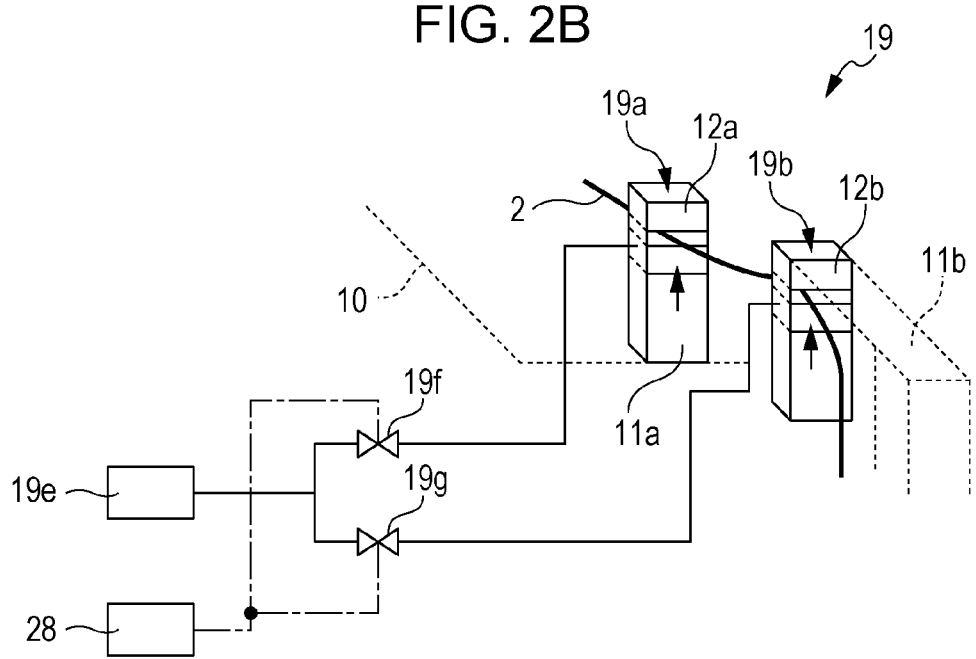
FIG. 2B illustrates the structure of the slave robot according to the first embodiment of the present disclosure.

As illustrated in FIGS. 2A and 2B and other drawings, the insertion apparatus 1 for a flexible elongate member includes at least a slave robot 19, which includes a first holding unit 19a and a second holding unit 19b, a direction angle detector 15s that functions as an example of an information acquiring unit, a position detector 19h that also functions as an example of an information acquiring unit, an operation information generator 9, and a slave controller 28 that functions as an example of an insertion operation controller.

As a more specific example, the insertion apparatus 1 includes a master robot 18, the slave robot 19, a determining unit 26, an X-ray imaging device 5, a monitor 8a, which is an example of a notifying unit 8, a force sensor 13, which is an example of a force detector, a control information database 24, an operation information database 17, and a database input/output unit 14.

When the operator 6 manipulates the master robot 18 to insert the guidewire 2, the slave robot 19 performs an operation for inserting the guidewire 2. The insertion operation includes insertion of the guidewire 2 into the blood vessel 3, stoppage of insertion or extraction of the guidewire 2, and extraction of the guidewire 2 from the blood vessel 3. Namely, "insertion apparatus for a flexible elongate member" may be interpreted as "apparatus for a flexible elongate member".

The slave robot 19 includes at least the first holding unit 19a and the second holding unit 19b. Each of the first holding unit 19a and the second holding unit 19b performs an opening/closing operation to hold or release the guidewire 2. The slave robot 19 inserts the guidewire 2 into the blood vessel 3 by moving the second holding unit 19b back and forth relative to the first holding unit 19a while controlling the time at which each of the first holding unit 19a and the second holding unit 19b holds and releases the guidewire 2.

The X-ray imaging device 5 captures an image of the blood vessel 3 or the guidewire 2 from the outside of the human body 4. The monitor 8a displays the image captured by the X-ray imaging device 5.

The second holding unit 19b is provided with the force sensor 13, which is an example of a force detector. The force sensor 13 measures a frictional force generated when the guidewire 2 comes into contact with a meandering portion or a branching portion of the blood vessel 3. When the determining unit 26 determines that stress is placed on the blood vessel 3 on the basis of the measurement information obtained by the force sensor 13, a warning is issued through the monitor 8a or a speaker 8b.

An input/output IF 7, which is connected to the database input/output unit 14, is an operation interface through which the operator 6 commands the insertion apparatus 1 to start or stop the insertion of the guidewire 2 into the blood vessel 3. The input/output IF 7 includes, for example, a button arranged on a side surface of the master robot 18.

Figure 3:
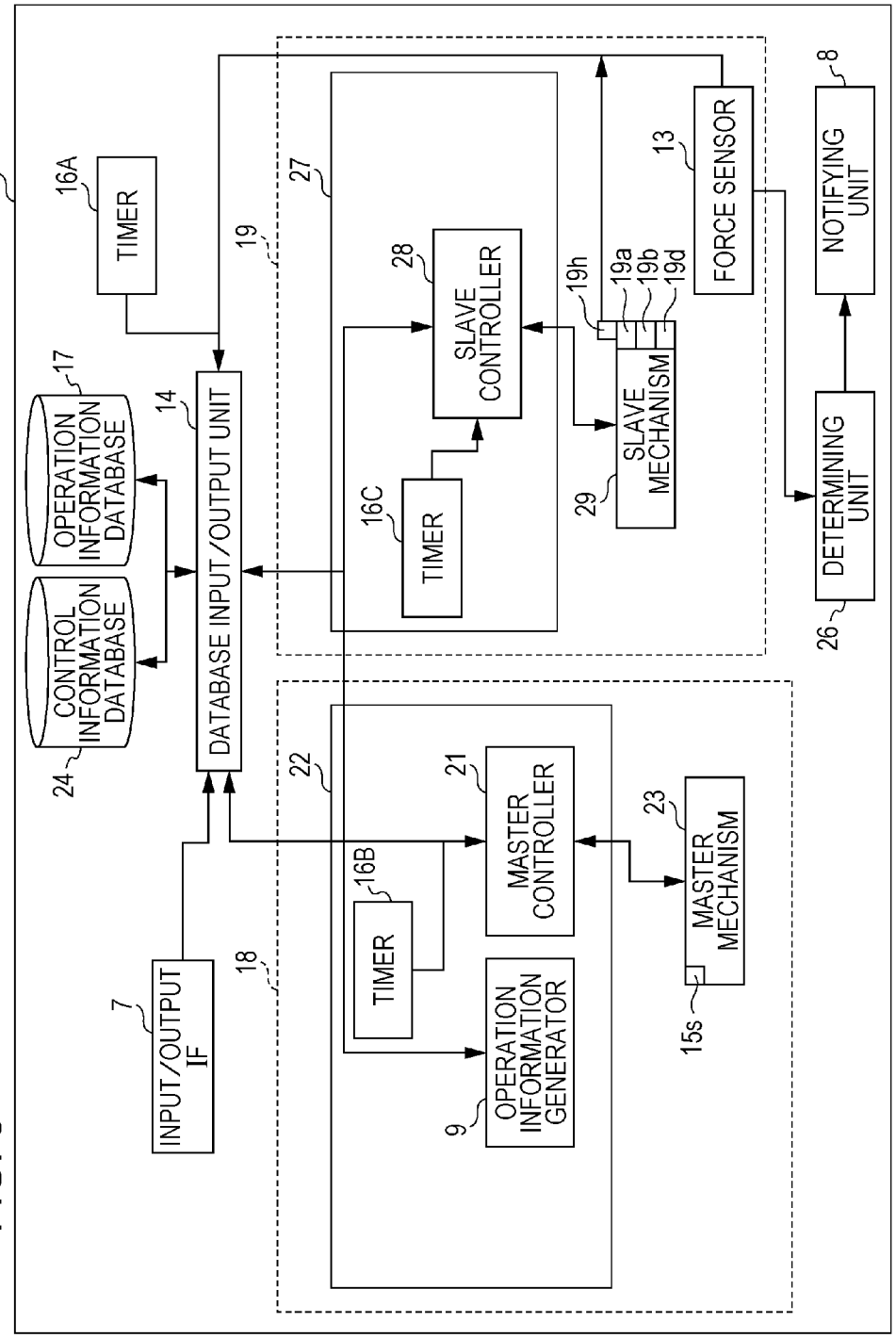
FIG. 3 is a block diagram illustrating the detailed structure of the insertion apparatus according to the first embodiment of the present disclosure.

FIG. 3 is a block diagram of the insertion apparatus 1.

Insertion Apparatus 1

As described above, the insertion apparatus 1 includes, for example, the master robot 18, the slave robot 19, the determining unit 26, the X-ray imaging device 5, the notifying unit 8, the force sensor 13, the control information database 24, the operation information database 17, and the database input/output unit 14.

The master robot 18 is a robot system which a person (an operator, a worker, etc.) manipulates by directly touching it. The slave robot 19 is a robot system that is separated from the master robot 18 and actually performs the insertion operation.

Master Robot 18

The master robot 18 is a robot system which a person manipulates by directly touching it, and includes at least a master mechanism 23 and a master control device 22.

Figure 4A:
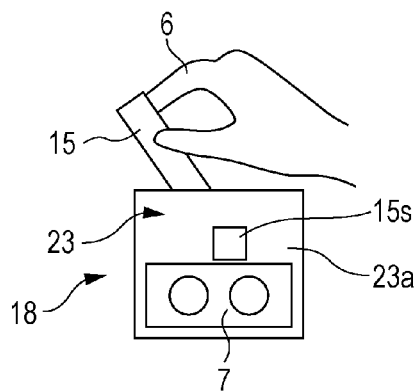
FIG. 4A illustrates the structure of a master robot according to the first embodiment of the present disclosure.

As illustrated in FIG. 4A, the master mechanism 23 includes, for example, a lever 15 that can be tilted forward and backward with respect to a master-mechanism base 23*a*. By using the lever 15, the operator 6 can input whether to move the guidewire 2 in an insertion direction or in a direction opposite to the insertion direction, and a speed of the movement. The lever 15 is provided with the direction angle detector 15*s*, which is capable of detecting the tilting direction and tilting angle of the lever 15, the tilting direction indicating an operation type, which is one of insertion, extraction, and stoppage. The direction angle detector 15*s* functions as an example of an information acquiring unit. The direction angle detector 15*s* detects the tilting direction and tilting angle of the lever 15. Information of the detection result is acquired by a master controller 21 at an operation timing determined by a timer 16B, and is stored in the operation information database 17 by the operation information generator 9. Thus, at least the information of the tilting angle of the lever 15, the tilting angle indicating the operation type, can be detected by the direction angle detector 15*s*. The direction angle detector 15*s* functions as an example of an information acquiring unit. The operation type is information used to distinguish between (1) insertion of the guidewire 2 into the blood vessel 3, (2) stoppage of insertion of the guidewire 2 into the blood vessel 3 and extraction of the guidewire 2 from the blood vessel 3, and (3) extraction of the guidewire 2 from the blood vessel 3.

Figure 4D:
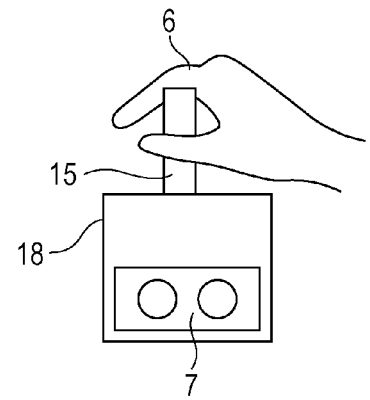
FIG. 4D illustrates the operation of the master robot according to the first embodiment of the present disclosure.
Figure 4B:
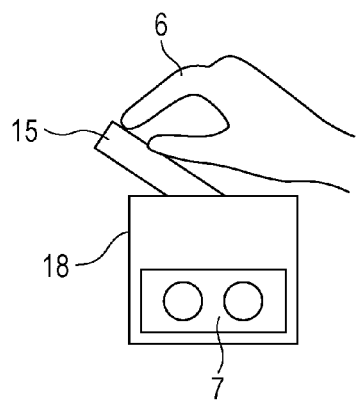
FIG. 4B illustrates the operation of the master robot according to the first embodiment of the present disclosure.
Figure 4E:
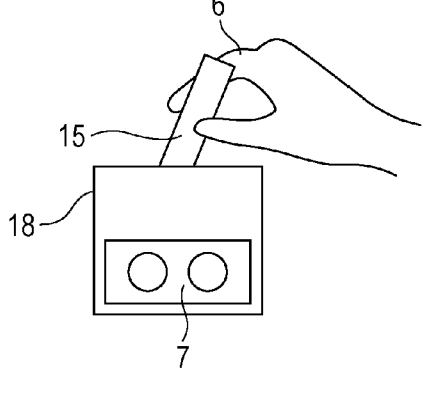
FIG. 4E illustrates the operation of the master robot according to the first embodiment of the present disclosure.
Figure 4C:
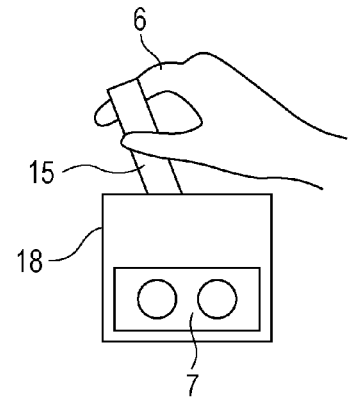
FIG. 4C illustrates the operation of the master robot according to the first embodiment of the present disclosure.
Figure 4F:
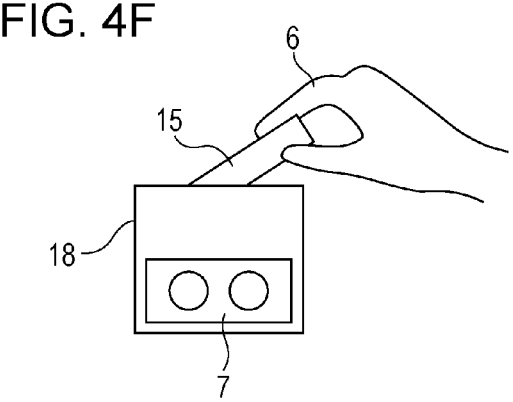
FIG. 4F illustrates the operation of the master robot according to the first embodiment of the present disclosure.

More specifically, when the lever 15 is tilted forward with respect to the master-mechanism base 23*a*, as illustrated in FIGS. 4B and 4C, the guidewire 2 is moved in the insertion direction and inserted into the blood vessel 3. When the lever 15 is tilted backward with respect to the master-mechanism base 23*a*, as illustrated in FIGS. 4E and 4F, the guidewire 2 is moved in the direction opposite to the insertion direction and extracted from the blood vessel 3. When the lever 15 is at the central neutral position, as illustrated in FIG. 4D, the movement of the guidewire 2 is stopped. The insertion speed of the guidewire 2 may be changed in accordance with the amount by which the lever 15 is tilted forward or backward. Here, "stoppage of the movement of the guidewire" may be interpreted as "stoppage of the operation of inserting the guidewire into the blood vessel". Alternatively, "stoppage of the movement of the guidewire" may be interpreted as "stoppage of the operation of extracting the guidewire from the blood vessel".

For example, in FIG. 4B, since the lever 15 is tilted forward by a large amount, the guidewire 2 is quickly inserted into the blood vessel 3. In FIG. 4C, since the lever 15 is tilted forward by a small amount, the guidewire 2 is slowly inserted into the blood vessel 3. In FIG. 4D, since the lever 15 is not tilted forward or backward and is at the neutral position (upright position), the insertion of the guidewire 2 into the blood vessel 3 is stopped. In FIG. 4E, since the lever 15 is tilted backward by a small amount, the guidewire 2 is slowly extracted from the blood vessel 3. In FIG. 4F, since the lever 15 is tilted backward by a large amount, the guidewire 2 is quickly extracted from the blood vessel 3. The speed at which the guidewire 2 is inserted or extracted is determined by using the control information database 24, which will be described below, on the basis of information of the tilting direction and tilting angle of the lever 15, which are detected by the direction angle detector 15*s*.

The input/output IF 7 is provided on a side surface of the master-mechanism base 23*a* of the master mechanism 23. The input/output IF 7 may include, for example, start and stop buttons for starting and stopping the insertion operation of the insertion apparatus 1.

The master control device 22 includes the master controller 21, the timer 16B, and the operation information generator 9. The master controller 21 acquires tilting angle information, which includes the tilting direction and tilting angle of the lever 15 included in the master mechanism 23 and which is detected by the direction angle detector 15*s*, at an operation timing determined by the timer 16B. The tilting angle information is stored in the operation information database 17, which will be described below, by the operation information generator 9. The tilting angle information may include an angle with a sign (+ or −) indicating whether the angle is greater or smaller than a certain angle.

Slave Robot 19

FIG. 2A illustrates the detailed structure of the slave robot 19. The slave robot 19 includes a slave mechanism 29, which includes the first holding unit 19*a*, the second holding unit 19*b*, and an insertion unit 19*c*, and a slave device 27, which includes the slave controller 28 and a timer 16C (see FIG. 3).

As illustrated in FIG. 2B, the first holding unit 19*a* includes a first support portion 11*a* and a first opening-and-closing portion 12*a*. The first support portion 11*a* is fixed to the table 10. The first opening-and-closing portion 12*a* is fixed to the first support portion 11*a* in such a manner that the first opening-and-closing portion 12*a* can be driven by an air supply 19*e*, which will be described below. For example, the first opening-and-closing portion 12*a* is an air chuck that is opened and closed by air supplied from the air supply 19*e* under the control of an air control valve 19*f*. The air chuck is a chuck mechanism that is opened and closed in response to introduction and removal of air. The guidewire 2 is held when the chuck mechanism is closed, and is released when the chuck mechanism is opened.

The second holding unit 19*b* includes a second support portion 11*b* and a second opening-and-closing portion 12*b*. One end of the second support portion 11*b* is fixed to a fixed portion 19*cb* of the insertion unit 19*c* (see FIG. 2A). The second opening-and-closing portion 12*b* is fixed to the second support portion 11*b*. The second opening-and-closing portion 12*b* is, for example, an air chuck that is opened and closed by air supplied from the air supply 19*e* under the control of an air control valve 19*g*. The air chuck is a chuck mechanism that is opened and closed in response to introduction and removal of air. The guidewire 2 is held when the chuck mechanism is closed, and is released when the chuck mechanism is opened. The slave controller 28 controls the operation of each of the air control valves 19*f* and 19*g*, and stores the information of the opened/closed state in the operation information database 17 through the database input/output unit 14.

As illustrated in FIG. 2A, the insertion unit 19*c* includes, for example, a single-axis stage which allows a movable portion 19*ca* to move with respect to the fixed portion 19*cb* in a single-axis direction, and a drive device 19*d*, such as a motor, which moves the movable portion 19ca back and forth with respect to the fixed portion 19cb. An example of the drive device 19d is a motor which rotates in forward and reverse directions so that a gear mechanism (not shown) moves the movable portion 19ca and the second support portion 11b, which is connected to the movable portion 19ca, with respect to the fixed portion 19cb.

Thus, the drive device 19d is capable of moving the second holding unit 19b back and force in the insertion direction of the guidewire 2 with respect to the fixed portion 19cb. The position of the movable portion 19ca with respect to the fixed portion 19cb indicates the position of the insertion unit 19c. More specifically, referring to FIG. 5, the insertion unit 19c includes the position detector 19h (see FIG. 2A), which is capable of detecting the position in a coordinate system in which the center of the fixed portion 19cb of the insertion unit 19c is at the origin (zero) and the insertion direction is the positive direction. The position detector 19h functions as an example of an information acquiring unit. The position information detected by the position detector 19h is stored in the operation information database 17 through the database input/output unit 14 together with time information obtained by a timer 16A at the detection time. Thus, the distance from the second holding unit 19b to a predetermined position that is near the first holding unit 19a can be detected by the position detector 19h. The position detector 19h functions as an example of an information acquiring unit.

Force Sensor 13

The force sensor 13 is fixed to one end of the second support portion 11b and includes, for example, a single-axis force sensor. For example, the force sensor 13 detects, through the second opening-and-closing portion 12b, a force generated when the guidewire 2 that has been inserted into the human body 4 from the outside comes into contact with the blood vessel 3 (force information). An example of a force sensor includes strain gauges disposed therein to detect forces in x, y, and z directions. Another example of a force sensor detects force with a piezoresistive element. When the force sensor 13 detects the force generated when the guidewire 2 that has been inserted into the human body 4 from the outside comes into contact with the blood vessel 3, the information detected by the force sensor 13 is stored in the operation information database 17 through the database input/output unit 14, and is input to the determining unit 26.

Next, an example of an operation of inserting the guidewire 2 performed by the slave robot 19 will be described.

FIGS. 6A to 6E illustrate the opened/closed states of the first opening-and-closing portion 12a and the second opening-and-closing portion 12b during the insertion of the guidewire 2.

Figure 6A:
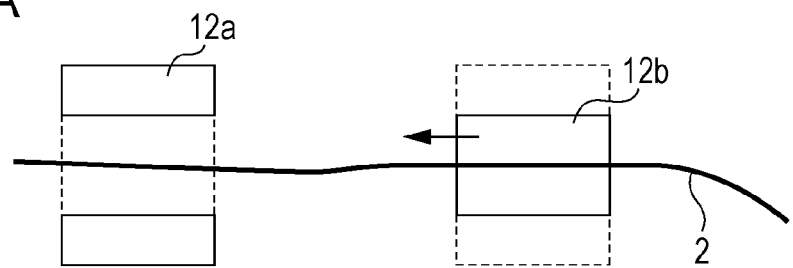
FIG. 6A illustrates the operation of a first opening-and-closing portion and a second opening-and-closing portion according to the first embodiment of the present disclosure.

When a command to insert the guidewire 2 into the blood vessel 3 in the insertion direction is input from the master robot 18 to the slave robot 19, first, as illustrated in FIG. 6A, the first opening-and-closing portion 12a is opened and the second opening-and-closing portion 12b is closed so that the guidewire 2 is held by the second opening-and-closing portion 12b. In response to the above-described command, the slave controller 28 starts an operation of controlling the opening-and-closing portions 12a and 12b.

Figure 6B:
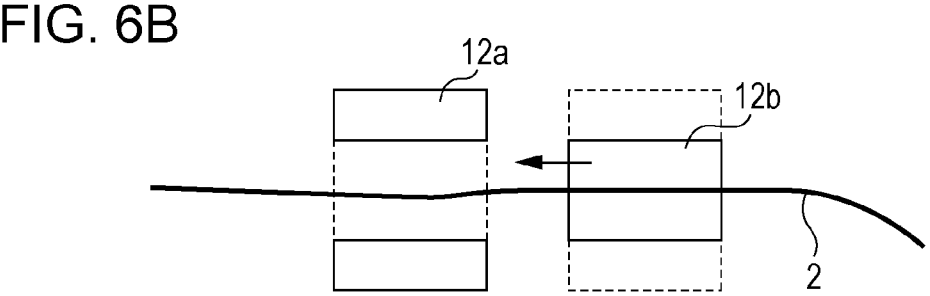
FIG. 6B illustrates the operation of the first opening-and-closing portion and the second opening-and-closing portion according to the first embodiment of the present disclosure.

Next, as illustrated in FIG. 6B, the drive device 19d drives the movable portion 19ca (see FIG. 2A) of the insertion unit 19c so as to move the second holding unit 19b including the second opening-and-closing portion 12b in the insertion direction by a predetermined amount while the first opening-and-closing portion 12a is opened and the guidewire 2 is held by the second opening-and-closing portion 12b, so that the guidewire 2 is inserted into the body (blood vessel). The predetermined amount is a distance such that the second opening-and-closing portion 12b approaches the first opening-and-closing portion 12a but does not come into contact with the first opening-and-closing portion 12a.

Figure 6C:
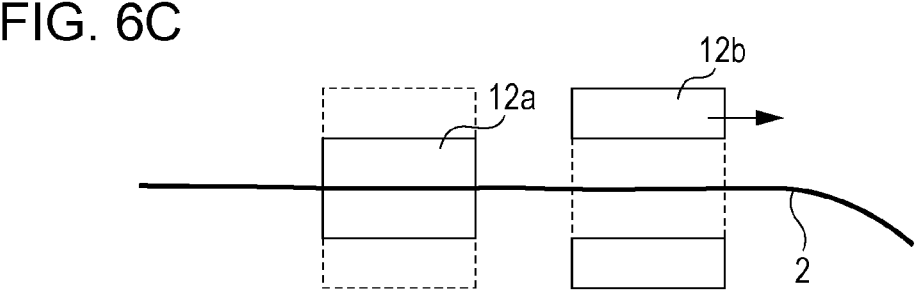
FIG. 6C illustrates the operation of the first opening-and-closing portion and the second opening-and-closing portion according to the first embodiment of the present disclosure.

Next, after the second holding unit 19b has been moved by the predetermined distance such that the second opening-and-closing portion 12b does not come into contact with the first opening-and-closing portion 12a, as illustrated in FIG. 6C, the first opening-and-closing portion 12a is closed and the second opening-and-closing portion 12b is opened, so that the guidewire 2 is held by the first opening-and-closing portion 12a. In this state, the drive device 19d drives the movable portion 19ca (see FIG. 2A) of the insertion unit 19c so as to move the second holding unit 19b including the second opening-and-closing portion 12b in the direction opposite to the insertion direction by, for example, the distance corresponding to the above-described predetermined amount.

Figure 6D:
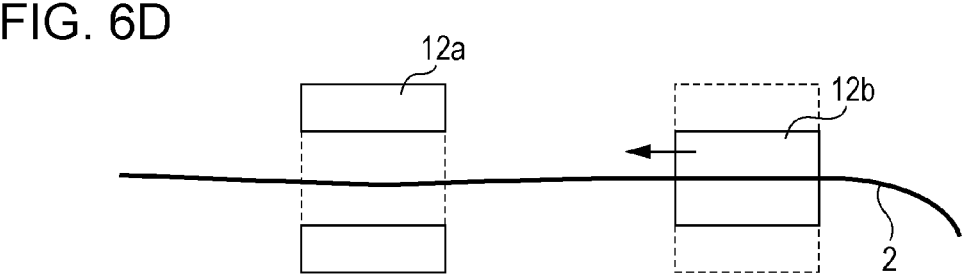
FIG. 6D illustrates the operation of the first opening-and-closing portion and the second opening-and-closing portion according to the first embodiment of the present disclosure.
Figure 6E:
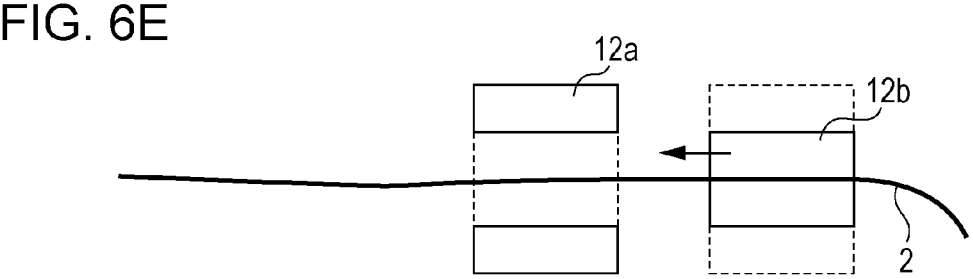
FIG. 6E illustrates the operation of the first opening-and-closing portion and the second opening-and-closing portion according to the first embodiment of the present disclosure.

Next, as illustrated in FIG. 6D, similar to FIGS. 6A and 6B, the drive device 19d drives the insertion unit 19c so as to move the second holding unit 19b in the insertion direction by the predetermined amount again while the first opening-and-closing portion 12a is opened and the second opening-and-closing portion 12b is closed. Accordingly, as illustrated in FIG. 6E, the guidewire 2 is inserted further into the body (blood vessel).

Database Input/Output Unit 14

The database input/output unit 14 independently inputs/outputs data to/from the operation information database 17, the control information database 24, the operation information generator 9 included in the master control device 22, the master controller 21 included in the master control device 22, the slave controller 28 included in the slave device 27, the force sensor 13, and the position detector 19h of the insertion unit 19c included in the slave robot 19.

Operation Information Database 17

The operation information database 17 stores operation information together with times by using the timer 16A. The operation information includes a master movement amount, which is obtained by converting, by using the control information database 24, the insertion speed information of the guidewire 2 into the amount of insertion of the guidewire 2 per unit time, the insertion speed information being detected by the direction angle detector 15s in response to the operation of tilting the lever 15 of the master mechanism 23. The operation information further includes position information of the movable portion 19ca of the slave robot 19 detected by the position detector 19h, information regarding an opening/closing operation of a chuck mechanism included in the first opening-and-closing portion 12a of the slave robot 19, information regarding an opening/closing operation of a chuck mechanism included in the second opening-and-closing portion 12b of the slave robot 19, and information regarding the force detected by the force sensor 13. The operation information is input to and output from the operation information database 17 through the database input/output unit 14.

FIG. 7 illustrates an example of the contents of the operation information stored in the operation information database 17.

(1) The Time column shows information regarding the time during the insertion operation. In the first embodiment, the time is expressed in terms of milliseconds (msec).

(2) The Operation Type column shows information regarding the type of operation. Here, "1" indicates the case in which the guidewire 2 is moved in the insertion direction, "2" indicates the case in which the guidewire 2 is moved in the direction opposite to the insertion direction, and "0" indicates the case in which the insertion is stopped.

(3) The Master Movement Amount column shows the master movement amount (amount of insertion of the guidewire 2) obtained by converting, by using the control information database 24 (see FIG. 8A), the insertion speed information of the guidewire 2 of the master mechanism 23 into the amount of movement of the guidewire 2 per unit time. For example, when the insertion speed of the guidewire 2 of the master mechanism 23 is v (m/msec), the master movement amount pm1 in a period from time t0 to time t1 is calculated as pm1=v×(t1−t0). In the first embodiment, the master movement amount is expressed in terms of meters (m).

Figure 5:
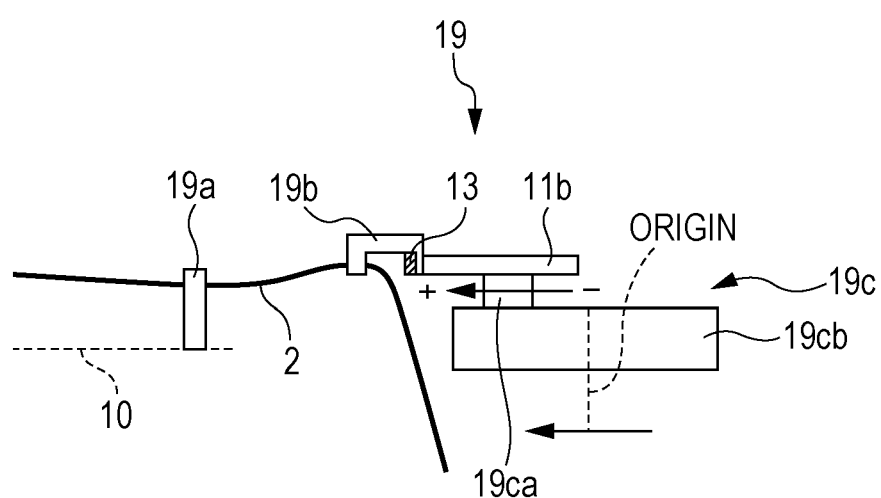
FIG. 5 illustrates the operation of an insertion unit according to the first embodiment of the present disclosure.

(4) The Position of Slave Insertion Unit column shows the position of the movable portion 19ca of the slave mechanism 29, more specifically, the position of the movable portion 19ca detected by the position detector 19h in a coordinate system in which the center of the insertion unit 19c is at the origin (zero) and the insertion direction is the positive direction, as illustrated in FIG. 5. In the first embodiment, the position is expressed in terms of meters (m).

(5) The First Opening-and-Closing Portion column shows the opened/closed state of the chuck mechanism of the first opening-and-closing portion 12a. Here, "1" indicates the state in which the chuck mechanism is closed, and "0" indicates the state in which the chuck mechanism is opened.

(6) The Second Opening-and-Closing Portion column shows the opened/closed state of the chuck mechanism of the second opening-and-closing portion 12b. Here, "1" indicates the state in which the chuck mechanism is closed, and "0" indicates the state in which the chuck mechanism is opened.

(7) The Force column shows the information of the force detected by the force sensor 13. In the first embodiment, the force is expressed in terms of Newton (N).

Control Information Database 24

The control information database 24 stores, as the control information, the information regarding the relationship between the tilting angle information and the speed information, the tilting angle information being detected by the direction angle detector 15s in response to the operation of tilting the lever 15 of the master mechanism 23. Therefore, the control information database 24 is used to calculate the insertion speed information of the guidewire 2, that is, the insertion speed of the master mechanism 23, on the basis of the tilting angle information detected by the direction angle detector 15s. In addition, the master movement amount is calculated by converting, by using the control information database 24, the insertion speed information of the guidewire 2 calculated by using the control information database 24 into the amount of insertion of the guidewire 2 per unit time. For example, when the insertion speed of the guidewire 2 of the master mechanism 23 in a period from time t0 to time t1 is v (m/msec), the master movement amount pm1 in the period from time t0 to time t1 is pm1=v×(t1−t0). Thus, the control information database 24 is used to calculate the insertion speed of the master mechanism 23, the insertion speed corresponding to the tilting angle information of the lever 15 of the master mechanism 23, and the amount of movement per unit time. The calculated insertion speed and the master movement amount are stored in the operation information database 17 by the operation information generator 9 as the operation information. The control information is input to and output from the control information database 24 through the database input/output unit 14.

Figures 8A, 8B:
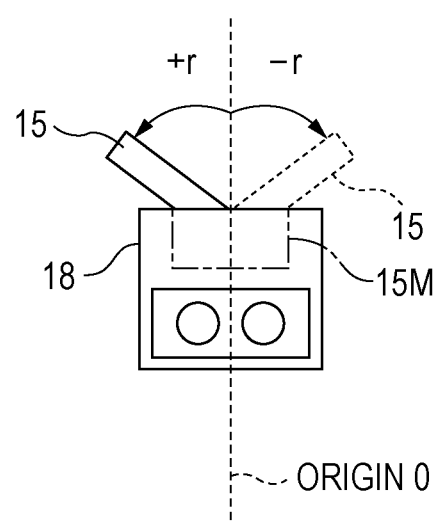
FIG. 8A illustrates a control information database according to the first embodiment of the present disclosure.
FIG. 8B illustrates the angle of a lever according to the first embodiment of the present disclosure.

FIG. 8A illustrates an example of the contents of the control information stored in the control information database 24.

(1) The Lever Angle column shows the tilting angle from the origin O illustrated in FIG. 8B. Referring to FIG. 8B, the plus sign indicates that the lever 15 is tilted leftward and the minus sign indicates that the lever 15 is tilted rightward. For example, the tilting angle may be determined in 11 steps in total, including 5 steps on the plus side, 5 steps on the minus side, and a step for the origin O. In the first embodiment, the tilting angle of the lever 15 is expressed in terms of radians.

(2) The Speed column shows the insertion speed of the guidewire 2 of the master mechanism 23. In the first embodiment, the speed is expressed in terms of m/msec.

With the control information stored in the control information database 24, when the tilting angle information is detected by the direction angle detector 15s in response to the operation of tilting the lever 15 of the master mechanism 23, the speed information can be calculated on the basis of the detected tilting angle information by using the control information database 24.

Timers 16A, 16B, and 16C

The timer 16A is used to activate the database input/output unit 14 every predetermined period (for example, every 4 msec) and input time information to the operation information database 17 when the operation information is generated.

The timer 16B is used to activate the master controller 21 every predetermined period (for example, every 4 msec).

The timer 16C is used to activate the slave controller 28 every predetermined period (for example, every 4 msec).

Operation Information Generator 9

The operation information generator 9 determines, by using the control information database 24, the insertion speed of the master mechanism 23 and the master movement amount per unit time on the basis of the tilting angle of the lever 15 detected by the direction angle detector 15s of the master mechanism 23 and the control information stored in the control information database 24. The operation information generator 9 stores the information determined by using the control information database 24 in the operation information database 17 as the operation information. The operation information generator 9 also generates, as the operation information, the information regarding the position of the movable portion 19ca of the slave mechanism 29, the information regarding the opened/closed state of the first opening-and-closing portion 12a (or the chuck mechanism thereof), and the information regarding the opened/closed state of the second opening-and-closing portion 12b (or the chuck mechanism thereof) on the basis of the master movement amount of the master mechanism 23 stored in the operation information database 17. The operation information generated by the operation information generator 9 is stored in the operation information database 17 through the database input/output unit 14. The operation information is, for example, information of an output of a signal indicating whether to open the first holding unit 19a to release the guidewire 2 or close the first holding unit 19a to hold the guidewire 2, and whether to close the second holding unit 19b to hold the guidewire 2 or open the second holding unit 19b to release the guidewire 2.

More specifically, the speed v of the master mechanism 23 is calculated by using the control information database 24 on the basis of the tilting angle r of the lever 15 from the origin O illustrated in FIG. 8B and the control information stored in the control information database 24 as illustrated in FIG. 8A (information regarding the relationship between the tilting angle r and the insertion speed v), the tilting angle r being acquired by the master controller 21 from the direction angle detector 15s. The master movement amount per unit time (for example, 1 msec) is determined by using the control information database 24 on the basis of the speed v calculated by the control information database 24. The speed v is positive when the lever 15 is tilted in the insertion direction, negative when the lever 15 is tilted in the direction opposite to the insertion direction, and zero when the lever 15 is in an upright position at the center. The master movement amount (pm0) determined by using the control information database 24 is stored in the operation information database 17 illustrated in FIG. 7 as the operation information together with time (t0).

The operation information generator 9 performs an operation of storing the operation information in the operation information database 17. This operation will now be described.

When the master movement amount is a positive value, that is, when the guidewire 2 is moved in the insertion direction as illustrated in FIGS. 6A and 6B, "1" is stored in the operation information database 17 as the operation type. In addition, the position Im0 calculated by adding the master movement amount pm0 to the current position Imbase of the movable portion 19ca (Im0=Imbase+pm0) is stored in the operation information database 17 together with time (t0) through the database input/output unit 14 as the operation information. In addition, when the guidewire 2 is moved in the insertion direction, as illustrated in FIG. 6A, the first opening-and-closing portion 12a is opened and the second opening-and-closing portion 12b is closed. Therefore, in the operation information database 17, "0" is stored in the column for the first opening-and-closing portion 12a and "1" is stored in the column for the second opening-and-closing portion 12b as the operation information.

As illustrated in FIG. 6C, after the guidewire 2 has been inserted by a predetermined amount, the movable portion 19ca is returned to the position before the insertion. Therefore, the position of the movable portion 19ca is set to Im1=Imbase. In addition, since the first opening-and-closing portion 12a is closed and the second opening-and-closing portion 12b is opened, "1" is stored in the column for the first opening-and-closing portion 12a and "0" is stored in the column for the second opening-and-closing portion 12b together with time (t1) as the operation information in the operation information database 17. The master movement amount stored in the operation information database 17 for time (t1) is 0.

Figure 6F:
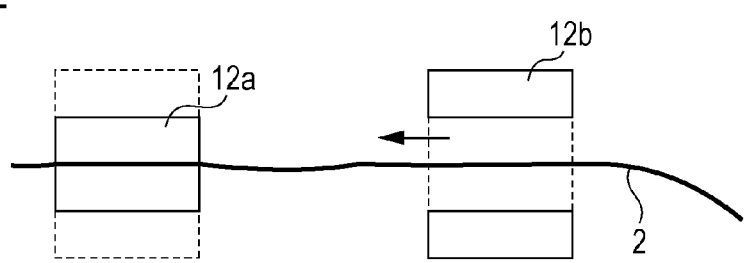
FIG. 6F illustrates the operation of the first opening-and-closing portion and the second opening-and-closing portion according to the first embodiment of the present disclosure.
Figure 6G:
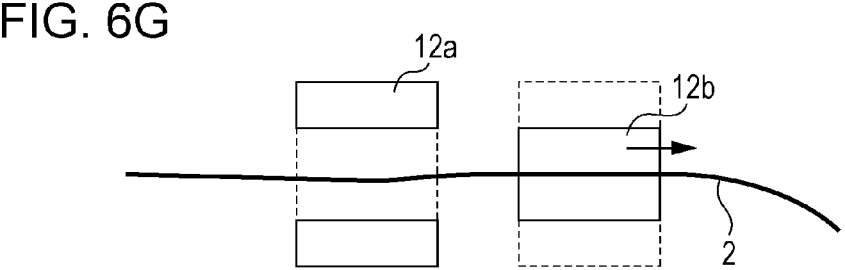
FIG. 6G illustrates the operation of the first opening-and-closing portion and the second opening-and-closing portion according to the first embodiment of the present disclosure.
Figure 6H:
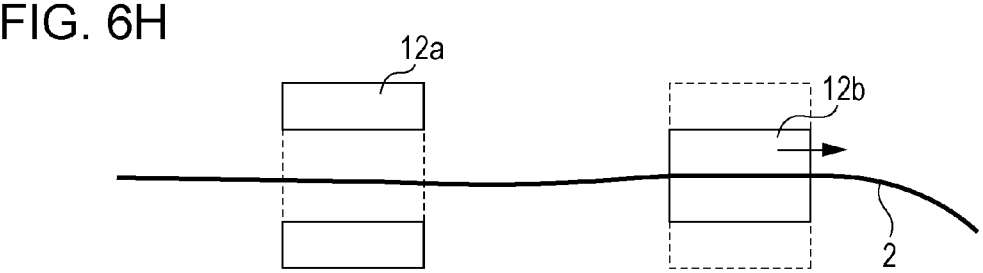
FIG. 6H illustrates the operation of the first opening-and-closing portion and the second opening-and-closing portion according to the first embodiment of the present disclosure.

When the master movement amount is a negative value, that is, when the guidewire 2 is moved in the direction opposite to the insertion direction as illustrated in FIGS. 6F to 6H, "2" is stored in the operation information database 17 as the operation type.

In addition, for the movement from the position shown in FIG. 6F to the position shown in FIG. 6G, as the operation information, a value obtained by adding a value obtained by inverting the master movement amount pm1 to a positive value to the position Imbase of the movable portion 19ca is stored as the operation information in the operation information database 17 as the position Im2 of the movable portion 19ca (Im2=Imbase+(−1×pm1)) together with time (t2). In addition, as illustrated in FIG. 6F, since the first opening-and-closing portion 12a is closed and the second opening-and-closing portion 12b is opened, "1" is stored in the column for the first opening-and-closing portion 12a and "0" is stored in the column for the second opening-and-closing portion 12b together with time (t2) as the operation information in the operation information database 17. The master movement amount stored in the operation information database 17 for time (t2) is 0.

Next, when the guidewire 2 is moved in the direction opposite to the insertion direction, as illustrated in FIG. 6G, the position of the movable portion 19ca is set to Im3=Imbase as the operation information. Since the first opening-and-closing portion 12a is opened and the second opening-and-closing portion 12b is closed, in the operation information database 17, "0" is stored in the column for the first opening-and-closing portion 12a and "1" is stored in the column for the second opening-and-closing portion 12b together with time (t3). The master movement amount (pm1) is stored together with time (t3) as the operation information in the operation information database 17.

Figure 6I:
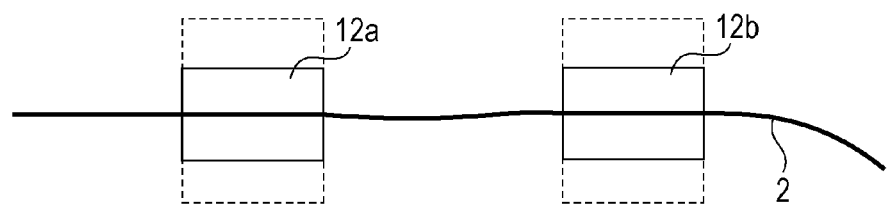
FIG. 6I illustrates the operation of the first opening-and-closing portion and the second opening-and-closing portion according to the first embodiment of the present disclosure.

When the master movement amount is 0, that is, when the slave robot 19 is to be stopped even if the master robot 18 is manipulated, "0" is stored in the operation information database 17 as the operation type. In addition, the master movement amount is set to 0, and the slave movement amount is set to the same value as that for the previous time. For example, as illustrated in FIG. 7, when the slave robot 19 is stopped at time t4, the master movement amount is set to 0. In addition, as the position of the movable portion 19ca of the slave mechanism 29, the same value as the position Im3 for the previous time t3 is stored in the operation information database 17 together with time t4. In addition, as illustrated in FIG. 6I, the first opening-and-closing portion 12a and the second opening-and-closing portion 12b are both closed to prevent the guidewire 2 from being moved accidentally. Therefore, "1" is set for both the first opening-and-closing portion 12a and the second opening-and-closing portion 12b in the operation information database 17.

In FIG. 6I, the first opening-and-closing portion 12a and the second opening-and-closing portion 12b are both closed to prevent the guidewire 2 from being moved accidentally. However, the second opening-and-closing portion 12b may be opened. In the case where the position of the movable portion 19ca generated by the operation information generator 9 is beyond the movable range of the movable portion 19ca, first, the movable portion 19ca may be moved to a position within the movable range, and then be moved by the remaining distance the next time. Alternatively, the movement by the remaining distance may be omitted.

Master Controller 21

The master controller 21 acquires the tilting angle information of the lever 15 from the direction angle detector 15s of the master mechanism 23 at an operation timing determined by the timer 16B, the tilting angle information being detected by the direction angle detector 15s. The operation information generator 9 stores the acquired information in the control information database 24 and the operation information database 17.

Slave Controller 28

The slave controller 28 controls the operation of each of the first holding unit 19a, the second holding unit 19b, and the insertion unit 19c on the basis of the operation information generated by the operation information generator 9.

Determining Unit 26

The determining unit 26 determines whether or not the value of the force detected by the force sensor 13 is greater than or equal to a predetermined stress detection threshold (for example, 0.5 N). When the value of the force detected by the force sensor 13 is greater than or equal to the predetermined stress detection threshold (for example, 0.5 N), the determining unit 26 determines that stress is placed on the blood vessel 3. The result of the determination performed by the determining unit 26 is output to the notifying unit 8 together with the force detected by the force sensor 13. When the value of the force detected by the force sensor 13 is less than the predetermined stress detection threshold (for example, 0.5 N), the determining unit 26 determines that no stress is applied to the blood vessel 3. In this case, the result of the determination may or may not be output to the notifying unit 8 together with the force detected by the force sensor 13.

It is not necessary that the determining unit 26 perform the determination each time the force is detected by the force sensor 13. The determining unit 26 may be such that it does not perform the determination in a certain period.

Figure 9A:
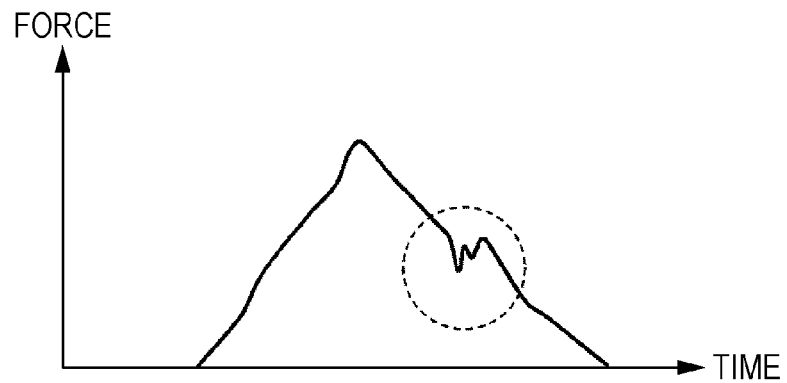
FIG. 9A is a graph showing force variation over time including a fluctuation due to switching between holding units according to the first embodiment of the present disclosure.
Figure 9B:
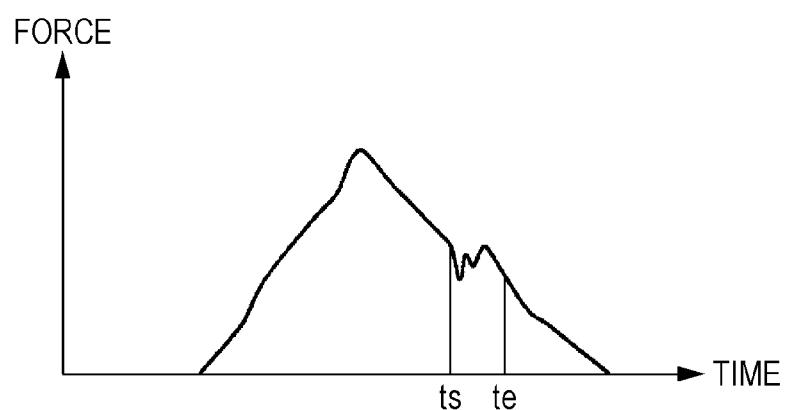
FIG. 9B is a graph showing force variation over time including the fluctuation due to switching between the holding units according to the first embodiment of the present disclosure.
Figure 9C:
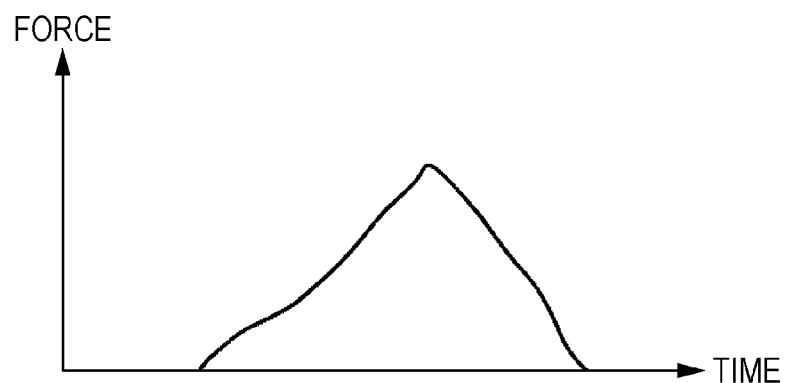
FIG. 9C is a graph showing force variation over time obtained when a process for preventing the fluctuation due to switching between the holding units is performed according to the first embodiment of the present disclosure.

FIG. 9A is a graph showing variation over time in the force applied when the guidewire 2 is being inserted into the blood vessel 3. When switching between the first holding unit 19a and the second holding unit 19b is performed to change the state shown in FIG. 6B to the state shown in FIG. 6C, there is a possibility that the force variation over time will fluctuate as in the region surrounded by the dashed circle in FIG. 9A. The fluctuation occurs when switching between the first holding unit 19a and the second holding unit 19b suddenly occurs. When such a fluctuation occurs, even if no stress is placed on the blood vessel 3 in practice, there is a risk that the value of the force detected by the force sensor 13 will be greater than or equal to the predetermined stress detection threshold (for example, 0.5 N) and it will be incorrectly determined that stress is placed on the blood vessel 3. To prevent the incorrect determination that stress is placed on the blood vessel 3 by the guidewire 2 when the force variation over time is fluctuating due to the influence of switching between the first holding unit 19a and the second holding unit 19b, the following process may be performed. For example, the determining unit 26 may determine that there is no stress for the force detected in a period from the time when a command to close the first holding unit 19a is issued (time "ts" in the graph of FIG. 9B) to the time after a certain duration of time (time "te" in the graph of FIG. 9B). In other words, the force variation in the period from time ts to time te may be omitted, and the determining unit 26 may determine whether or not there is stress on the basis of the value of the force detected by the force sensor 13 in the period from time t0 to time ts and the period from time te. In this case, as illustrated in FIG. 9C, the fluctuation in the force variation over time caused by the switching between the holding units can be eliminated from the graph showing the force variation over time. A similar process may be performed when the state shown in FIG. 6C is changed to the state shown in FIG. 6D and when the state shown in FIG. 6F is changed to the state shown in FIG. 6G. In such a case, the above-described incorrect determination can be prevented.

Notifying Unit 8

The notifying unit 8 is a device that notifies the operator of the result of the determination performed by the determining unit 26, and includes, for example, the monitor 8a.

Figure 10:
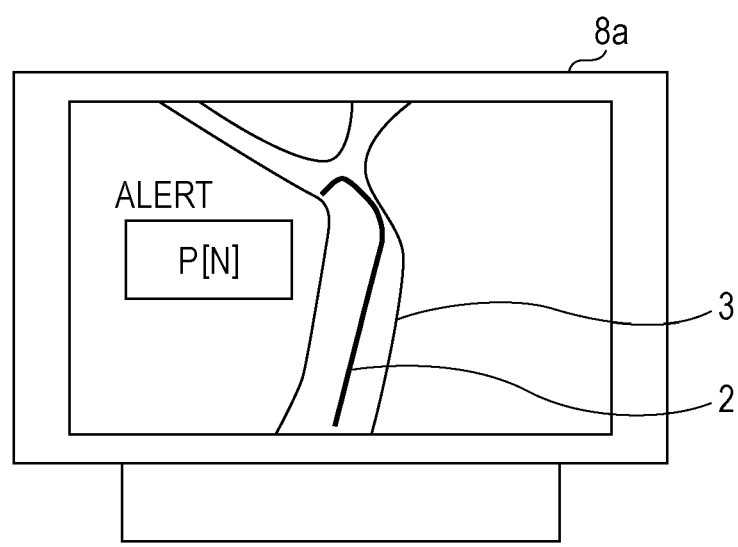
FIG. 10 illustrates an example of a notifying unit according to the first embodiment of the present disclosure.

More specifically, as in the monitor 8a illustrated in FIG. 10, the force P [N] detected by the force sensor 13 may be displayed together with the X-ray image. When the determining unit 26 determines that stress is placed on the blood vessel 3, a warning, such as a message "ALERT", may be additionally displayed.

In addition, when the determining unit 26 determines that stress is placed on the blood vessel 3, the speaker 8b may emit a warning sound to warn the operator 6.

Figure 11:
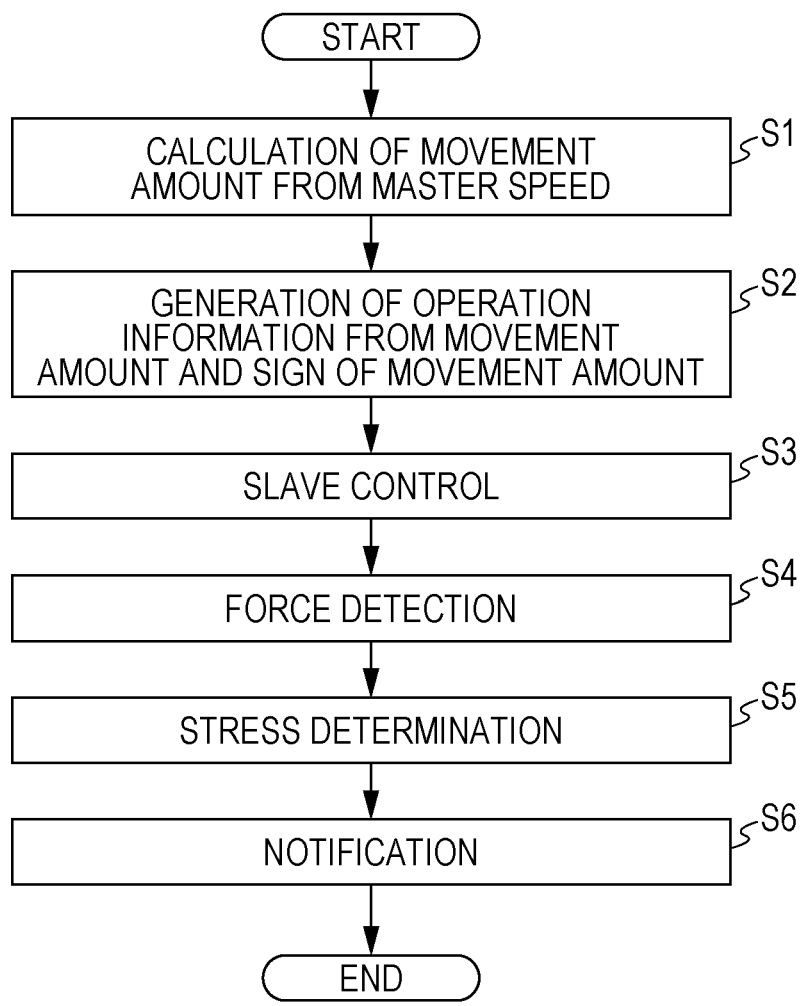
FIG. 11 is a flowchart for the insertion apparatus according to the first embodiment of the present disclosure.

Next, the operation steps carried out by the insertion apparatus 1 according to the first embodiment will be described. FIG. 11 is a flowchart for the insertion apparatus 1 according to the first embodiment.

When a command to start the insertion is issued through the input/output IF 7, in Step S1, the operation information generator 9 calculates the insertion speed of the master mechanism 23 by using the control information database 24. More specifically, the operation information generator 9 acquires the tilting angle of the lever 15, the tilting angle being detected by the direction angle detector 15s of the master mechanism 23 through the master controller 21, and the control information stored in the control information database 24 (information regarding the relationship between the tilting angle r and the speed v). Then, the operation information generator 9 calculates the insertion speed on the basis of the acquired tilting angle and the control information stored in the control information database 24. The operation information generator 9 also calculates the amount of movement per unit time as the master movement amount on the basis of the calculated insertion speed. The operation information generator 9 stores the calculated insertion speed and master movement amount in the operation information database 17 as the operation information.

Next, in Step S2, the operation information generator 9 generates the operation information including the position of the movable portion 19ca, the opened/closed state of the first opening-and-closing portion 12a, and the opened/closed state of the second opening-and-closing portion 12b on the basis of the master movement amount of the master mechanism 23 stored in the operation information database 17, the sign of the master movement amount, and the operation type acquired by the direction angle detector 15s. The generated operation information is stored in the operation information database 17 together with time.

Next, in Step S3, the slave controller 28 controls the operation of each of the first holding unit 19a, the second holding unit 19b, and the insertion unit 19c of the slave mechanism 29 on the basis of the operation information generated by the operation information generator 9.

Next, in Step S4, the force sensor 13 detects the force applied to the guidewire 2 while the slave mechanism 29 is in operation.

Next, in Step S5, the determining unit 26 determines whether or not stress is placed on the blood vessel 3 on the basis of the detection value obtained by the force sensor 13.

Next, in Step S6, when the determining unit 26 has determined that stress is placed on the blood vessel 3 on the basis of the detection value obtained by the force sensor 13, the result of the determination is presented to the operator 6 through the monitor 8a or the speaker 8b. When the determining unit 26 has determined that stress is not placed on the blood vessel 3 on the basis of the detection value obtained by the force sensor 13, the result of the determination may or may not be presented to the operator 6 through the monitor 8a or the speaker 8b.

After that, when a command to end the insertion is issued through the input/output IF 7, the insertion is ended. When no command to end the insertion is issued, Steps S1 to S6 are repeated.

Effects of First Embodiment

As described above, according to the first embodiment, the slave robot 19 includes the first holding unit 19a, the second holding unit 19b, and the insertion unit 19c. By controlling the operation of each of the first holding unit 19a, the second holding unit 19b, and the insertion unit 19c, the force applied when a flexible elongate member is inserted can be detected by using a known strain gauge or the like. Thus, the operation of inserting the flexible elongate member can be assisted by using a robot or the like.

Second Embodiment

Figure 12:
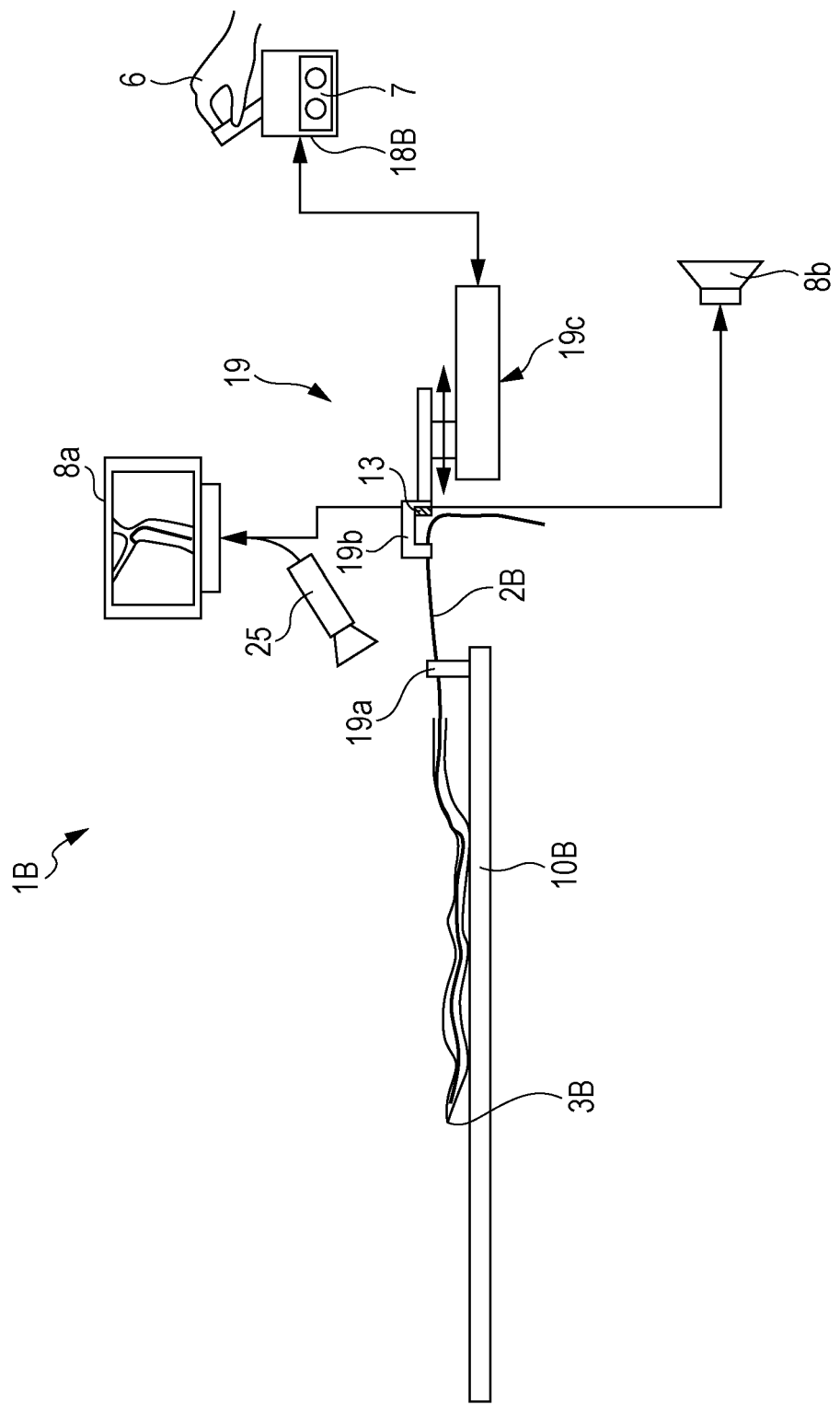
FIG. 12 illustrates the outline of the structure of an insertion apparatus according to a second embodiment of the present disclosure.

According to a second embodiment of the present disclosure, as illustrated in FIG. 12, an insertion apparatus 1B for a flexible elongate member is used to insert an optical fiber 2B through a fiber tube 3B as an example of insertion of a flexible elongate member performed in a factory.

In the insertion apparatus 1B for a flexible elongate member according to the second embodiment of the present disclosure, the basic structures of a slave robot 19, a determining unit 26, an X-ray imaging device 5, a monitor 8a that functions as an example of a notifying unit, a force sensor 13 that functions as an example of a force detector, a control information database 24, an operation information database 17, and a database input/output unit 14 are similar to those in the first embodiment. Therefore, description of common features is omitted, and differences from the first embodiment will be described in detail. The major difference from the first embodiment is a master control device 22B included in a master robot 18B. This will be described in detail.

FIG. 12 illustrates the outline of the insertion apparatus 1B used to insert the optical fiber 2B, which is an example of a flexible elongate member in a factory, through the fiber tube 3B placed on a table 10B.

An operator 6, that is, a worker, issues a command through the master robot 18B so that the slave robot 19 performs an operation of inserting the optical fiber 2B through the fiber tube 3B. Similar to the first embodiment, the slave robot 19 inserts the optical fiber 2B through the fiber tube 3B while controlling, in accordance with the manipulation by the operator 6, that is, the worker, the timing at which each of a first holding unit 19a and a second holding unit 19b holds and releases the optical fiber 2B, and the movement of a movable portion 19ca by using the slave controller 28. The first holding unit 19a and the second holding unit 19b open and close respective chuck mechanisms.

While the operator 6, that is, the worker, is performing the operation of inserting the optical fiber 2B, an image of a region around the fiber tube 3B is captured by an imaging device 25, and the image captured by the imaging device 25 is displayed on the monitor 8a.

The second holding unit 19b is provided with the force sensor 13. The force sensor 13 measures a frictional force generated when the optical fiber 2B comes into contact with a meandering portion of the fiber tube 3B, and the force measured by the force sensor 13 is presented to the operator 6, that is, the worker, through the monitor 8a or the like. When the determining unit 26 determines that the force measured by the force sensor 13 is greater than or equal to a predetermined stress detection threshold, the determining unit 26 issues a warning through the monitor 8a or a speaker 8b. An input/output IF 7 is an operation interface through which a command to start or stop the insertion apparatus 1B is issued, and is, for example, a button. The input/output IF 7 is arranged on, for example, a side surface of the master robot 18B.

Figure 13:
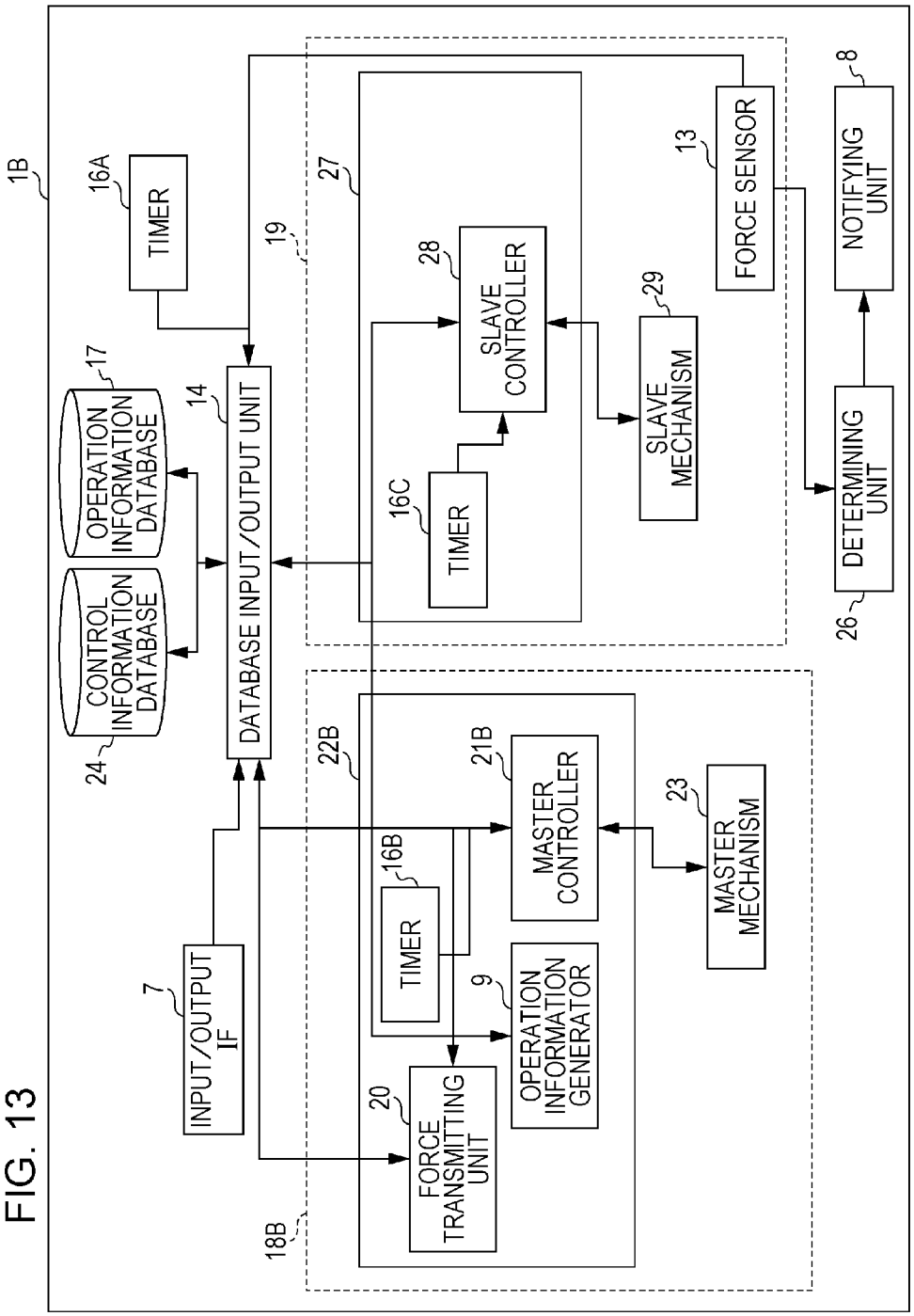
FIG. 13 is a block diagram illustrating the detailed structure of the insertion apparatus according to the second embodiment of the present disclosure.

FIG. 13 is a block diagram of the insertion apparatus 1B according to the second embodiment.

Master Robot 18B

The master robot 18B includes components similar to those in the first embodiment, and further includes a force transmitting unit 20 in the master control device 22B. The force transmitting unit 20 transmits force to the hand of the operator 6, that is, the worker, under the control of a master controller 21B on the basis of the force information detected by the force sensor 13 of the slave robot 19. An example of the force transmitting unit 20 includes a motor 15M used to rotate a lever 15 illustrated in FIG. 8B, and controls the motor 15M by using the force information detected by the force sensor 13 as a target command value.

Database Input/Output Unit 14

The database input/output unit 14 independently inputs/outputs data to/from the operation information database 17, the control information database 24, an operation information generator 9, the master controller 21B, the force sensor 13, and the force transmitting unit 20.

Operation Information Generator 9

Similar to the first embodiment, the operation information generator 9 determines, by using the control information database 24, the insertion speed of the master mechanism 23 and the master movement amount (amount of movement of the optical fiber 2B) per unit time on the basis of the tilting angle of the lever 15 detected by the direction angle detector 15s of the master mechanism 23 and the control information stored in the control information database 24. The operation information generator 9 stores the information determined by using the control information database 24 in the operation information database 17 as the operation information. The operation information generator 9 also generates, as the operation information, the information regarding the position of the movable portion 19ca of the slave mechanism 29, the information regarding the opened/closed state of the first opening-and-closing portion 12a (or the chuck mechanism thereof), and the information regarding the opened/closed state of the second opening-and-closing portion 12b (or the chuck mechanism thereof) on the basis of the master movement amount of the master mechanism 23 stored in the operation information database 17. The operation information generated by the operation information generator 9 is stored in the operation information database 17 through the database input/output unit 14.

More specifically, the speed v of the master mechanism 23 is calculated by using the control information database 24 on the basis of the tilting angle r of the lever 15 from the origin O illustrated in FIG. 8B and the control information stored in the control information database 24 as illustrated in FIG. 8A (information regarding the relationship between the tilting angle r and the insertion speed v), the tilting angle r being acquired by the master controller 21 from the direction angle detector 15s. The master movement amount per unit time (for example, 1 msec) is determined by using the control information database 24 on the basis of the speed v calculated by the control information database 24. The speed v is positive when the lever 15 is tilted in the insertion direction, negative when the lever 15 is tilted in the direction opposite to the insertion direction, and zero when the lever 15 is in an upright position at the center. The master movement amount (pm0) determined by using the control information database 24 is stored in the operation information database 17 illustrated in FIG. 14 as the operation information together with time (t0).

The operation information generator 9 performs an operation of storing the operation information in the operation information database 17. This operation will now be described.

Figure 15A:
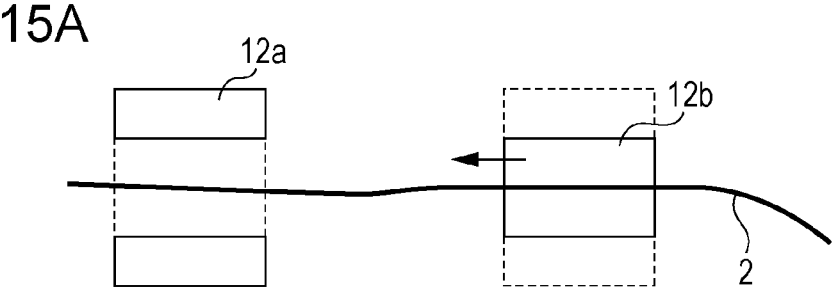
FIG. 15A illustrates the operation of a first opening-and-closing portion and a second opening-and-closing portion according to the second embodiment of the present disclosure.
Figure 15B:
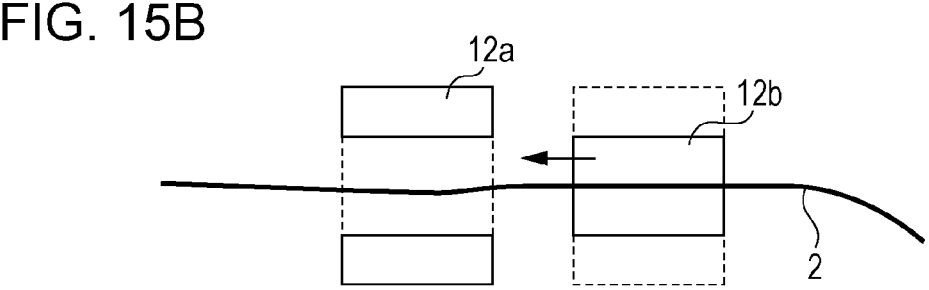
FIG. 15B illustrates the operation of the first opening-and-closing portion and the second opening-and-closing portion according to the second embodiment of the present disclosure.

When the master movement amount is a positive value, that is, when the optical fiber 2B is moved in the insertion direction as illustrated in FIGS. 15A and 15B, "1" is stored in the operation information database 17 as the operation type. In addition, similar to the first embodiment, the position Im0 calculated by adding the master movement amount pm0 to the current position Imbase of the movable portion 19ca (Im0=Imbase+pm0) is stored in the operation information database 17 together with time (t0) through the database input/output unit 14 as the operation information. In addition, when the optical fiber 2B is moved in the insertion direction, as illustrated in FIG. 15A, the first opening-and-closing portion 12a is opened and the second opening-and-closing portion 12b is closed. Therefore, in the operation information database 17, "0" is stored in the column for the first opening-and-closing portion 12a and "1" is stored in the column for the second opening-and-closing portion 12b as the operation information.

Figure 15C:
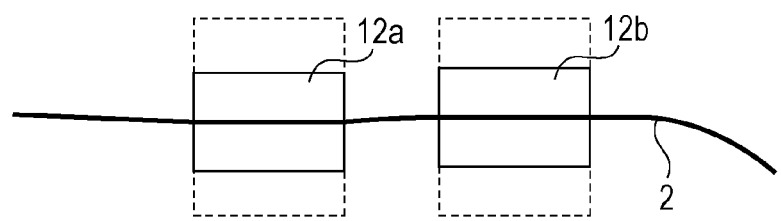
FIG. 15C illustrates the operation of the first opening-and-closing portion and the second opening-and-closing portion according to the second embodiment of the present disclosure.
Figure 15D:
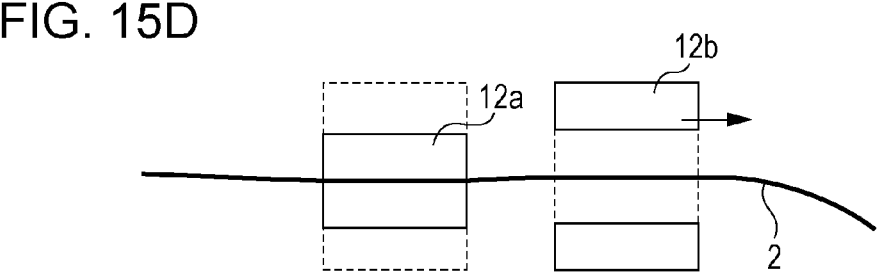
FIG. 15D illustrates the operation of the first opening-and-closing portion and the second opening-and-closing portion according to the second embodiment of the present disclosure.
Figure 15E:
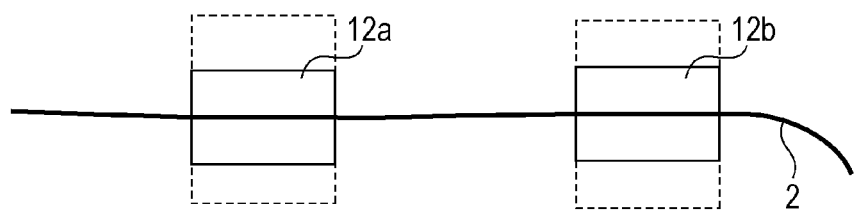
FIG. 15E illustrates the operation of the first opening-and-closing portion and the second opening-and-closing portion according to the second embodiment of the present disclosure.
Figure 15F:
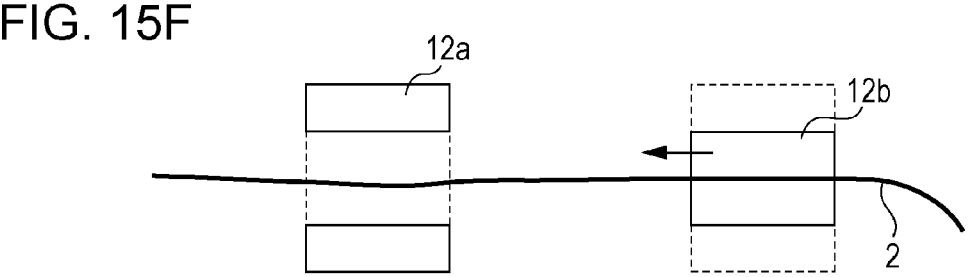
FIG. 15F illustrates the operation of the first opening-and-closing portion and the second opening-and-closing portion according to the second embodiment of the present disclosure.

Next, as illustrated in FIG. 15D, after the optical fiber 2B has been inserted by a predetermined amount, when the movable portion 19ca is moved to the position before the insertion, the first opening-and-closing portion 12a is closed and the second opening-and-closing portion 12b is opened simultaneously in the first embodiment. However, since the first opening-and-closing portion 12a and the second opening-and-closing portion 12b are respectively closed and opened simultaneously, there is a risk that the optical fiber 2B will be moved accidentally in the opening/closing process. Accordingly, stress may be placed on the optical fiber 2B or the fiber tube 3B in the opening/closing process. For example, there is a possibility that force variation over time will fluctuate as in the region surrounded by the dashed circle in FIG. 9A. Accordingly, in the second embodiment, operation information for causing the first opening-and-closing portion 12a and the second opening-and-closing portion 12b to be closed at the same time, as illustrated in FIG. 15C, before the state shown in FIG. 15D is established is stored in the operation information database 17 by the operation information generator 9. By carrying out such an operation based on the operation information, as described below, the optical fiber 2B can be prevented from being moved accidentally. As a result, a graph of force variation over time including no fluctuation, as illustrated in FIG. 9C, can be obtained. More specifically, the operation information generator 9 stores in the operation information database 17, together with time t1, the operation information in which the master movement amount at time t1 is 0 and the position of the movable portion 19ca of the slave mechanism 29 at time t1 is the same as the position Im0 at time t0. In addition, the first opening-and-closing portion 12a and the second opening-and-closing portion 12b are both set to the closed state, and "1" is stored in both the column for the first opening-and-closing portion 12a and the column for the second opening-and-closing portion 12b as the operation information in the operation information database 17.

Next, as illustrated in FIG. 15D, after the optical fiber 2B has been inserted by a predetermined amount, the movable portion 19ca is returned to the position before the insertion. Therefore, the position of the movable portion 19ca is set to Im1=Imbase. In addition, since the first opening-and-closing portion 12a is closed and the second opening-and-closing portion 12b is opened, "1" is stored in the column for the first opening-and-closing portion 12a and "0" is stored in the column for the second opening-and-closing portion 12b together with time (t2) as the operation information in the operation information database 17. The master movement amount stored in the operation information database 17 for time (t2) is 0.

Figure 15G:
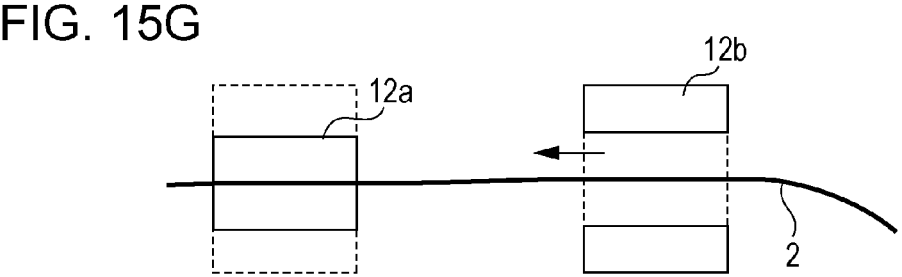
FIG. 15G illustrates the operation of the first opening-and-closing portion and the second opening-and-closing portion according to the second embodiment of the present disclosure.
Figure 15H:
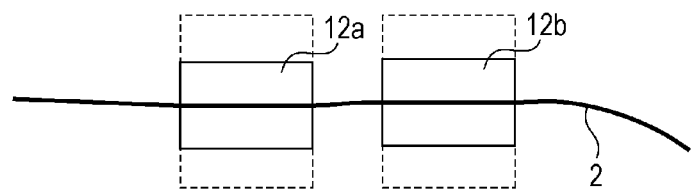
FIG. 15H illustrates the operation of the first opening-and-closing portion and the second opening-and-closing portion according to the second embodiment of the present disclosure.
Figure 15I:
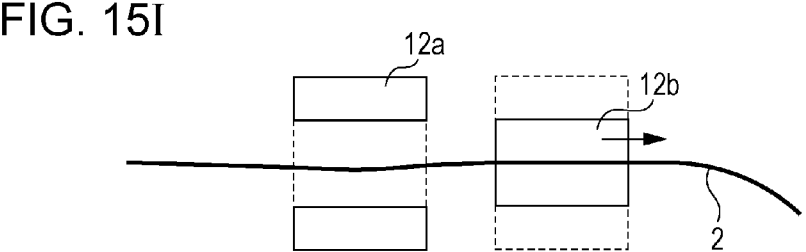
FIG. 15I illustrates the operation of the first opening-and-closing portion and the second opening-and-closing portion according to the second embodiment of the present disclosure.
Figure 15J:
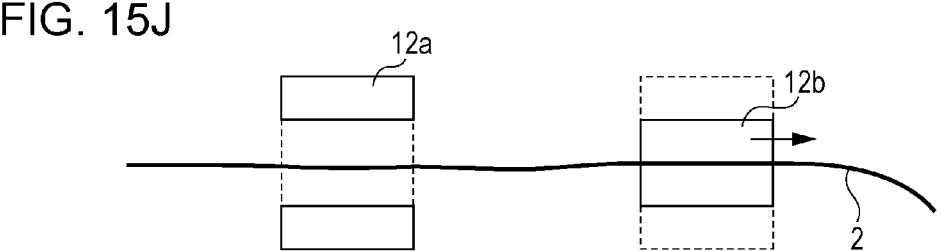
FIG. 15J illustrates the operation of the first opening-and-closing portion and the second opening-and-closing portion according to the second embodiment of the present disclosure.

When the master movement amount is a negative value, that is, when the optical fiber 2B is moved in the direction opposite to the insertion direction as illustrated in FIGS. 15G to 15I, "2" is stored in the operation information database 17 as the operation type.

In FIG. 15I, when the first opening-and-closing portion 12a is opened and the second opening-and-closing portion 12b is closed simultaneously, there is a risk that the optical fiber 2B will be moved and stress will be placed on the optical fiber 2B or the fiber tube 3B. Therefore, an operation of closing both the first opening-and-closing portion 12a and the second opening-and-closing portion 12b at the same time, as illustrated in FIG. 15H, may be carried out before the state shown in FIG. 15I is established. In such a case, the optical fiber 2B may be moved from being moved accidentally.

First, as illustrated in FIG. 15G, a value obtained by adding a value obtained by inverting the master movement amount pm1 to a positive value to the position Imbase of the movable portion 19ca is stored in the operation information database 17 as the position Im2 of the movable portion 19ca (Im2=Imbase+(−1×pm1)) together with time (t3).

In addition, as illustrated in FIG. 15G, since the first opening-and-closing portion 12a is closed and the second opening-and-closing portion 12b is opened, "1" is stored in the column for the first opening-and-closing portion 12a and "0" is stored in the column for the second opening-and-closing portion 12b together with time (t3) as the operation information in the operation information database 17. The master movement amount stored in the operation information database 17 for time (t3) is 0.

Next, as illustrated in FIG. 15H, the first opening-and-closing portion 12a and the second opening-and-closing portion 12b are both closed at the same time. Accordingly, "1" is stored in both the column for the first opening-and-closing portion 12a and the column for the second opening-and-closing portion 12b together with time (t4) as the operation information in the operation information database 17. In addition, the operation information in which the master movement amount at time t4 is 0 and the position of the movable portion 19ca of the slave mechanism 29 at time t4 is the same as the position Im2 at time t3 is stored in the operation information database 17 together with time t4.

Next, when the optical fiber 2B is moved in the direction opposite to the insertion direction, as illustrated in FIG. 15I, the position Im3 of the movable portion 19ca is set to Im3=Imbase as the operation information. Since the first opening-and-closing portion 12a is opened and the second opening-and-closing portion 12b is closed, in the operation information database 17, "0" is stored in the column for the first opening-and-closing portion 12a and "1" is stored in the column for the second opening-and-closing portion 12b together with time (t5). The master movement amount (pm1) is stored together with time (t5) in the operation information database 17.

Figure 15K:
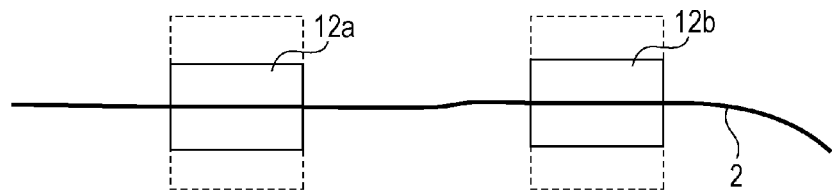
FIG. 15K illustrates the operation of the first opening-and-closing portion and the second opening-and-closing portion according to the second embodiment of the present disclosure.

When the master movement amount is 0, that is, when the slave robot 19 is to be stopped even when the master robot 18B is manipulated, an operation illustrated in FIG. 15K, which is similar to the operation illustrated in FIG. 6I in the first embodiment, is performed. Since the operation is similar to that in the first embodiment, description thereof is omitted.

Master Controller 21

The master controller 21 acquires the tilting angle information of the lever 15 from the direction angle detector 15s of the master mechanism 23 at an operation timing determined by the timer 16B, the tilting angle information being detected by the direction angle detector 15s. The operation information generator 9 stores the acquired information in the control information database 24 and the operation information database 17. In addition, the master controller 21 performs control for transmitting force to the operator 6, that is, the worker, on the basis of the force detected by the force detector in response to a command issued by the force transmitting unit 20.

Next, the operation steps carried out by the insertion apparatus 1B according to the second embodiment will be described. FIG. 16 is a flowchart for the insertion apparatus 1B according to the second embodiment.

When a command to start the insertion is issued through the input/output IF 7, in Step S11, the operation information generator 9 calculates the insertion speed of the master mechanism 23 by using the control information database 24. More specifically, the operation information generator 9 acquires the tilting angle of the lever 15, the tilting angle being detected by the direction angle detector 15s of the master mechanism 23 through the master controller 21, and the control information stored in the control information database 24 (information regarding the relationship between the tilting angle r and the speed v). Then, the operation information generator 9 calculates the insertion speed on the basis of the acquired tilting angle and the control information stored in the control information database 24. The operation information generator 9 also calculates the amount of movement per unit time as the master movement amount on the basis of the calculated insertion speed. The operation information generator 9 stores the calculated insertion speed and master movement amount in the operation information database 17 as the operation information.

Next, in Step S12, the operation information generator 9 generates the operation information of the position of the movable portion 19ca, the opened/closed state of the first opening-and-closing portion 12a, and the opened/closed state of the second opening-and-closing portion 12b on the basis of the master movement amount of the master mechanism 23 stored in the operation information database 17, the sign of the master movement amount, and the operation type acquired by the direction angle detector 15s. The generated operation information is stored in the operation information database 17 together with time.

Next, in Step S13, the slave controller 28 controls the operation of each of the first holding unit 19a, the second holding unit 19b, and the insertion unit 19c of the slave mechanism 29 on the basis of the operation information generated by the operation information generator 9.

Next, in Step S14, the force sensor 13 detects the force applied to the optical fiber 2B while the slave mechanism 29 is in operation.

Next, in Step S15, the determining unit 26 determines whether or not stress is placed on the optical fiber 2B or the fiber tube 3B on the basis of the detection value obtained by the force sensor 13.

Next, in Step S16, when the determining unit 26 has determined that stress is placed on the optical fiber 2B or the fiber tube 3B on the basis of the detection value obtained by the force sensor 13, the result of the determination is presented to the operator 6, that is, the worker, through the monitor 8a or the speaker 8b. When the determining unit 26 has determined that stress is not placed on the optical fiber 2B or the fiber tube 3B on the basis of the detection value obtained by the force sensor 13, the result of the determination may or may not be presented to the operator 6, that is, the worker, through the monitor 8a or the speaker 8b.

Next, in Step S17, the force transmitting unit 20 determines the force to be presented to the operator 6, that is, the worker, on the basis of the force information detected by the force sensor 13 of the slave robot 19. The master controller 21 controls the operation of the master mechanism 23 so that the master mechanism 23 transmits the force to be presented to the operator 6, that is, the worker.

After that, when a command to end the insertion is issued through the input/output IF 7, the insertion is ended. When no command to end the insertion is issued, Steps S11 to S17 are repeated.

Effects of Second Embodiment

As described above, since the force transmitting unit 20 is provided, the operator 6, that is, the worker, can perform the operation while sensing a force with their hand when the flexible elongate member is inserted. Thus, the operation of inserting the flexible elongate member can be assisted by using a robot or the like.

Third Embodiment

The outline of an insertion apparatus 1C for a flexible elongate member according to a third embodiment will be described.

Similar to the first embodiment, FIG. 17 illustrates a catheter test or treatment in which an operator 6 inserts a guidewire 2, which is an example of a flexible elongate member, into a human body 4 from the outside. The guidewire 2 is inserted toward an affected part of a blood vessel 3, which is an example of a tube, of a brain or heart of the human body 4.

In the third embodiment, the operator 6 holds a second holding unit 19b, which is a component of the insertion apparatus 1C, with their hand and moves the second holding unit 19b forward and backward along the insertion direction. The insertion apparatus 1C automatically holds and releases the guidewire 2 to insert the guidewire 2.

The insertion apparatus 1C according to the third embodiment differs from the insertion apparatus 1 according to the first embodiment in that the master robot is omitted and the structure is that of the slave robot 19. In other words, the insertion apparatus 1C includes a robot 19C for inserting the flexible elongate member, a determining unit 26, an X-ray imaging device 5, a monitor 8a, which is an example of a notifying unit 8, a force sensor 13, which is an example of a force detector, a control information database 24, an operation information database 17, a database input/output unit 14, and a distance detector 30.

Similar to the first embodiment, the robot 19C includes an insertion operation mechanism 29C, which has a structure and function similar to those of the slave mechanism 29 according to the first embodiment, and an insertion operation device 27C, which is similar to the slave device 27 according to the first embodiment. The insertion operation mechanism 29C includes at least a first holding unit 19a and the second holding unit 19b. A specific example of the robot 19C includes an insertion unit 19c in addition to the above-described constituent elements. The insertion operation device 27C includes an insertion operation controller 28C similar to the slave controller 28 according to the first embodiment, a timer 16C, and an operation information generator 9C that corresponds to the operation information generator 9 included in the master control device 22 according to the first embodiment. The insertion operation controller 28C performs a determination based on the relationship between a distance L detected by the distance detector 30 and a predetermined opening/closing control threshold, and controls the opening/closing operations of the first holding unit 19a and the second holding unit 19b on the basis of the result of the determination.

The operator 6 directly holds the robot 19C to insert the guidewire 2.

The robot 19C inserts the guidewire 2 while controlling the timing at which each of the first holding unit 19a and the second holding unit 19b, which open and close, holds and releases the guidewire 2 in accordance with the operation performed by the operator 6.

While the operator 6 is performing the operation of inserting the guidewire 2, the X-ray imaging device 5 captures an image of the blood vessel 3 or the guidewire 2 from the outside of the human body 4. The monitor 8a displays the image captured by the X-ray imaging device 5.

The second holding unit 19b is provided with the force sensor 13, which is an example of a force detector. The force sensor 13 measures a frictional force generated when the guidewire 2 comes into contact with a meandering portion or a branching portion of the blood vessel 3. When the determining unit 26 determines that stress is placed on the blood vessel 3 on the basis of the measurement information obtained by the force sensor 13, a warning is issued through the monitor 8a or a speaker 8b.

An input/output IF 7, which is connected to the database input/output unit 14, is an operation interface through which a command to start or stop the insertion apparatus 1 and an operation type, which is one of insertion in an insertion direction, extraction in a direction opposite to the insertion direction, and stoppage, are input. The input/output IF 7 is, for example, a button arranged on a side surface of the table 10.

Figure 18:
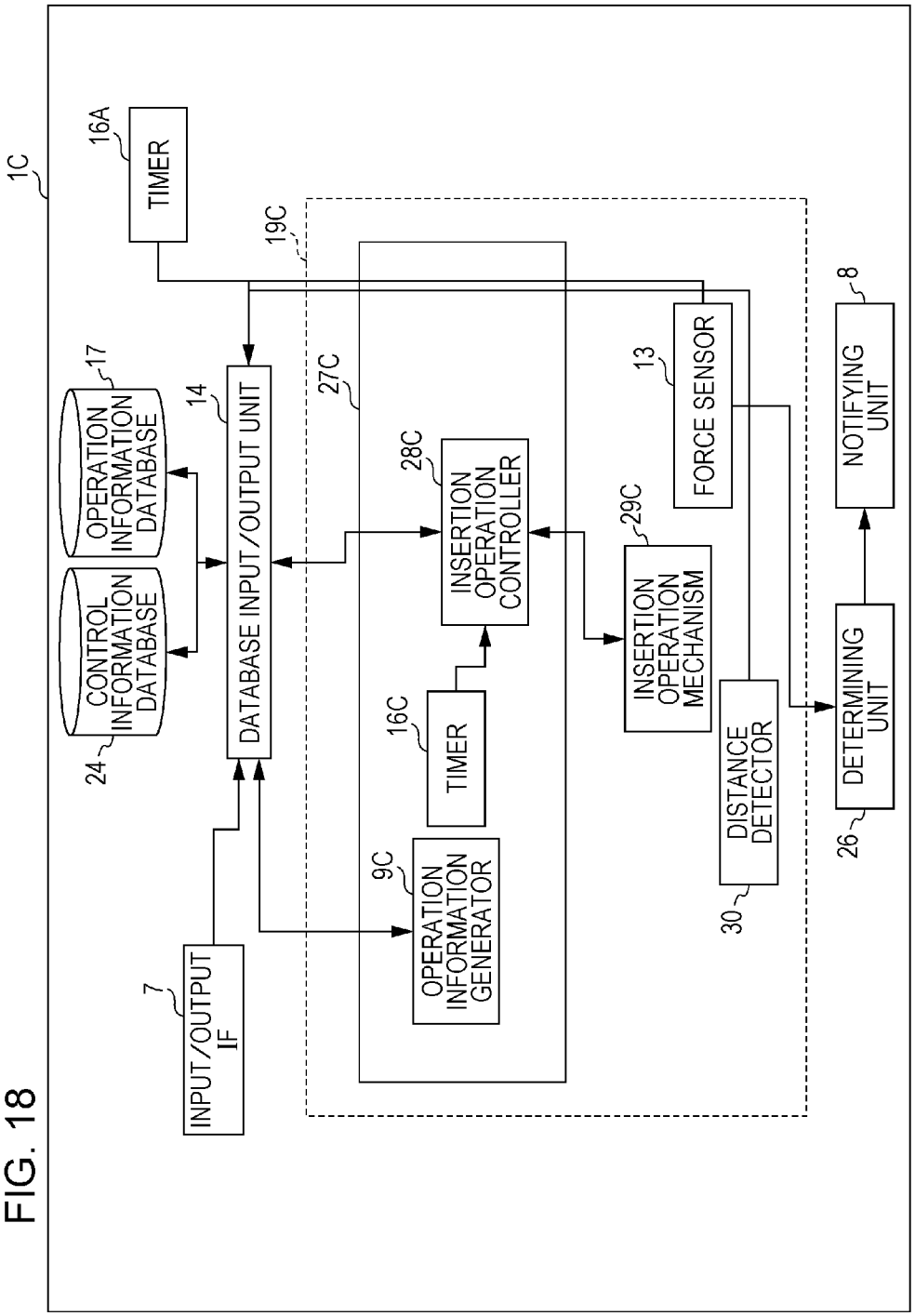
FIG. 18 is a block diagram illustrating the detailed structure of the insertion apparatus according to the third embodiment of the present disclosure.

FIG. 18 is a block diagram of the insertion apparatus 1C.
Insertion Apparatus 1C As described above, the insertion apparatus 1C includes, for example, the robot 19C, the determining unit 26, the X-ray imaging device 5, the notifying unit 8, the force sensor 13, the control information database 24, the operation information database 17, the database input/output unit 14, and the distance detector 30.
Robot 19C The robot 19C is a robot system which a person manipulates by directly touching it, and inserts the guidewire 2 in accordance with the manipulation by the person.

Figure 19A:
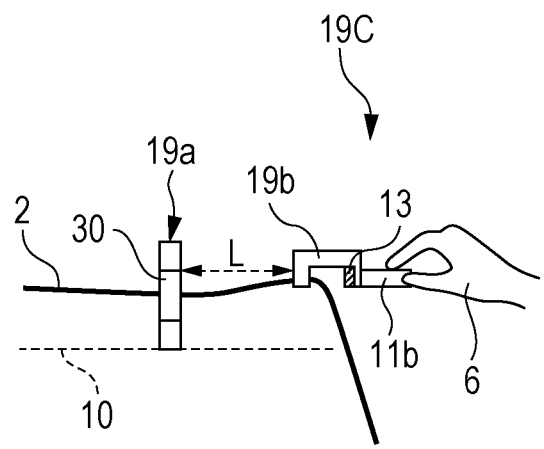
FIG. 19A illustrates the structure of a slave robot according to the third embodiment of the present disclosure.

FIG. 19A illustrates the detailed structure of the robot 19C. The robot 19C includes the insertion operation mechanism 29C, which includes the first holding unit 19a and the second holding unit 19b, and the insertion operation device 27C, which includes the insertion operation controller 28C, the timer 16C, and the operation information generator 9C.

Figure 19B:
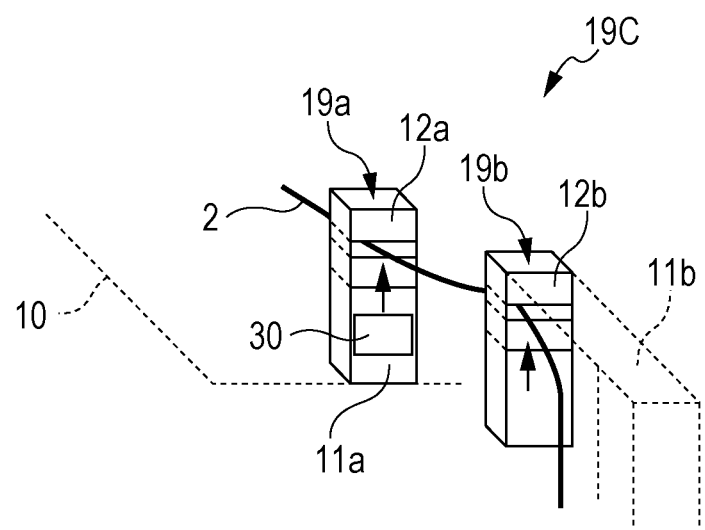
FIG. 19B illustrates the structure of the slave robot according to the third embodiment of the present disclosure.

As illustrated in FIG. 19B, the first holding unit 19a includes a first support portion 11a and a first opening-and-closing portion 12a. The first support portion 11a is fixed to the table 10. The first opening-and-closing portion 12a is fixed to the first support portion 11a. For example, similar to the first embodiment, the first opening-and-closing portion 12a is an air chuck that is opened and closed by air supplied from the air supply 19e under the control of an air control valve 19f. The air chuck is a chuck mechanism that is opened and closed in response to introduction and removal of air. The guidewire 2 is held when the chuck mechanism is closed, and is released when the chuck mechanism is opened.

The second holding unit 19b includes a second support portion 11b and a second opening-and-closing portion 12b. One end of the second support portion 11b can be held by the operator 6 by hand. The second opening-and-closing portion 12b is fixed to an end of the second support portion 11b. Similar to the first embodiment, the second opening-and-closing portion 12b is, for example, an air chuck that is opened and closed by air supplied from the air supply 19e under the control of an air control valve 19g. The air chuck is a chuck mechanism that is opened and closed in response to introduction and removal of air. The guidewire 2 is held when the chuck mechanism is closed, and is released when the chuck mechanism is opened. The insertion operation controller 28C controls the operation of each of the air control valves 19f and 19g, and stores the information of the opened/closed state in the operation information database 17 through the database input/output unit 14.

The insertion apparatus 1C does not include the insertion unit 19c according to the first embodiment.
Distance Detector 30

As illustrated in FIG. 19A, the distance detector 30 is arranged, for example, on the first holding unit 19a. The distance detector 30 is a distance sensor which intermittently measures the distance L between the first holding unit 19a and the second holding unit 19b (for example, once every predetermined time period).

Next, an example of an operation of inserting the guidewire 2 performed by the robot 19C will be described.

FIGS. 20A to 20E illustrate the opened/closed states of the first opening-and-closing portion 12a and the second opening-and-closing portion 12b while the guidewire 2 is being inserted.

Figure 20A:
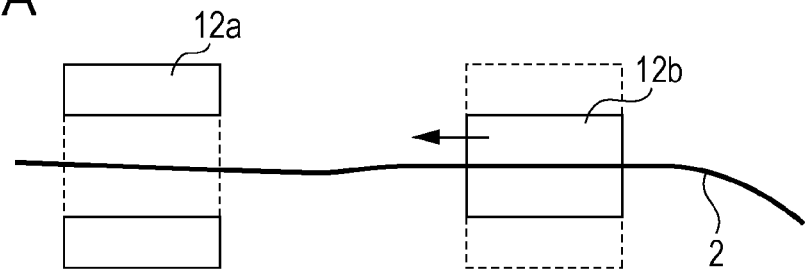
FIG. 20A illustrates the operation of a first opening-and-closing portion and a second opening-and-closing portion according to the third embodiment of the present disclosure.

Assume that the operator 6 has issued a command for insertion in the insertion direction to the insertion apparatus 1C through the input/output IF 7. In this case, first, as illustrated in FIG. 20A, the operator 6 holds the second opening-and-closing portion 12b by hand and moves the second opening-and-closing portion 12b away from the first opening-and-closing portion 12a (in the direction opposite to the insertion direction) while the first opening-and-closing portion 12a and the second opening-and-closing portion 12b are both opened. When the insertion operation controller 28C determines that the distance L detected by the distance detector 30 has become greater than or equal to a predetermined first threshold (first opening/closing control threshold) L1, the second opening-and-closing portion 12b is closed while the first opening-and-closing portion 12a is opened under the control of the insertion operation controller 28C, as illustrated in FIG. 20A. Thus, the guidewire 2 is held by the second opening-and-closing portion 12b.

Figure 20B:
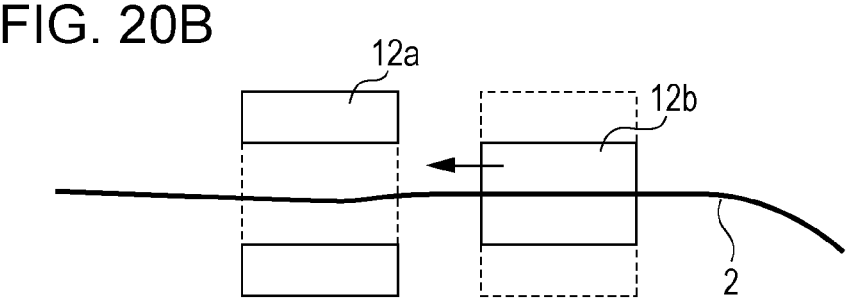
FIG. 20B illustrates the operation of the first opening-and-closing portion and the second opening-and-closing portion according to the third embodiment of the present disclosure.

Next, as illustrated in FIG. 20B, the operator 6 holds the second opening-and-closing portion 12b by hand and moves the second opening-and-closing portion 12b in the insertion direction while the guidewire 2 is held by the second opening-and-closing portion 12b. Thus, the guidewire 2 is inserted into the body.

Figure 20C:
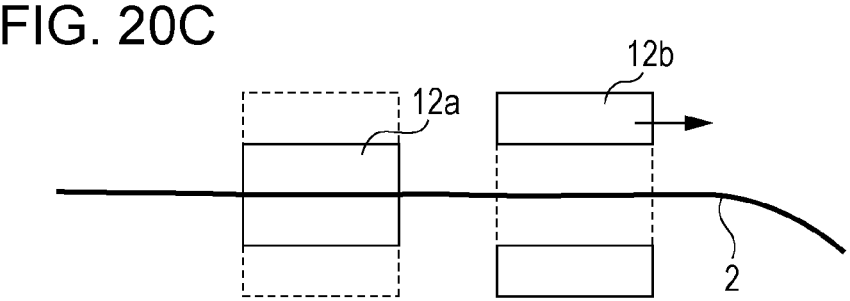
FIG. 20C illustrates the operation of the first opening-and-closing portion and the second opening-and-closing portion according to the third embodiment of the present disclosure.

Next, when the insertion operation controller 28C determines that the distance L detected by the distance detector 30 has become smaller than or equal to a predetermined second threshold (second opening/closing control threshold) L2, the first opening-and-closing portion 12a is closed and the second opening-and-closing portion 12b is opened, as illustrated in FIG. 20C, under the control of the insertion operation controller 28C. Thus, the guidewire 2 is held by the first opening-and-closing portion 12a. In this state, the operator 6 holds the second holding unit 19b by hand and moves the second holding unit 19b in the direction opposite to the insertion direction.

Figure 20D:
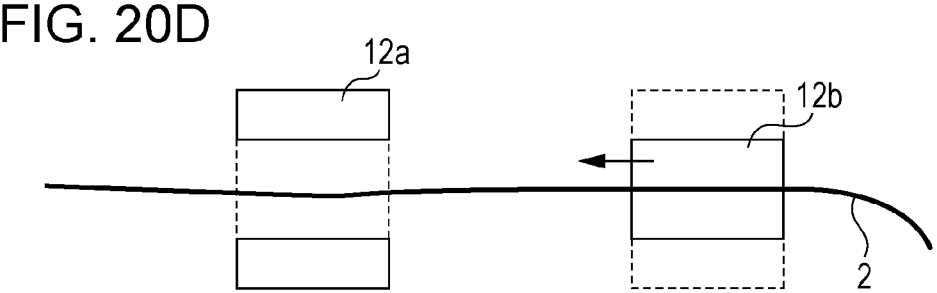
FIG. 20D illustrates the operation of the first opening-and-closing portion and the second opening-and-closing portion according to the third embodiment of the present disclosure.
Figure 20E:
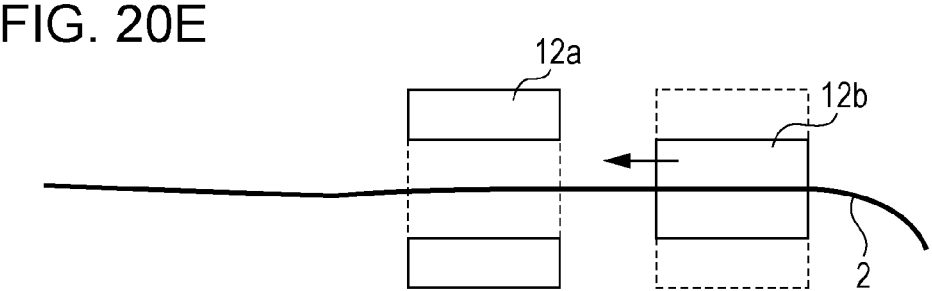
FIG. 20E illustrates the operation of the first opening-and-closing portion and the second opening-and-closing portion according to the third embodiment of the present disclosure.

Next, when the insertion operation controller 28C determines that the distance L detected by the distance detector 30 has become greater than or equal to the predetermined first threshold L1, the first opening-and-closing portion 12a is opened and the second opening-and-closing portion 12b is closed, as illustrated in FIG. 20D. In this state, the operator 6 moves the second holding unit 19b in the insertion direction to insert the guidewire 2 further into the body, as illustrated in FIG. 20E.

Database Input/Output Unit 14

The database input/output unit 14 independently inputs/outputs data to/from the operation information database 17, the control information database 24, the operation information generator 9C, the insertion operation controller 28C, the force sensor 13, and the distance detector 30.

Operation Information Database 17

The operation information database 17 stores operation information together with times by using the timer 16A. The operation information includes the distance between the first holding unit 19a and the second holding unit 19b detected by the distance detector 30; information regarding an opening/closing operation of the first opening-and-closing portion 12a performed by the robot 19C; information regarding an opening/closing operation of the second opening-and-closing portion 12b performed by the robot 19C; and information regarding the force detected by the force sensor 13. The operation information is input to and output from the operation information database 17 through the database input/output unit 14.

FIG. 21 illustrates an example of the contents of the operation information stored in the operation information database 17.

(1) The Time column shows information regarding the time during the insertion operation. In the third embodiment, the time is expressed in terms of milliseconds (msec).

(2) The Operation Type column shows information regarding the type of operation. Here, "1" indicates the case in which the guidewire 2 is moved in the insertion direction, "2" indicates the case in which the guidewire 2 is moved in the direction opposite to the insertion direction, and "0" indicates the case in which the insertion is stopped.

(3) The Distance column shows the distance between the first holding unit 19a and the second holding unit 19b detected by the distance detector 30. In the third embodiment, the distance is expressed in terms of meters (m).

(4) The First Opening-and-Closing Portion column shows the opened/closed state of the chuck mechanism of the first opening-and-closing portion 12a. Here, "1" indicates the state in which the chuck mechanism is closed, and "0" indicates the state in which the chuck mechanism is opened.

(5) The Second Opening-and-Closing Portion column shows the opened/closed state of the second opening-and-closing portion 12b. Here, "1" indicates the state in which the chuck mechanism is closed, and "0" indicates the state in which the chuck mechanism is opened.

(6) The Force column shows the information of the force detected by the force sensor 13. In the third embodiment, the force is expressed in terms of Newton (N).

Control Information Database 24

The control information database 24 stores information regarding thresholds used to determine the opened/closed states of the first opening-and-closing portion 12a and the second opening-and-closing portion 12b as control information. The control information is input to and output from the control information database 24 through the database input/output unit 14.

Figures 23, 24:
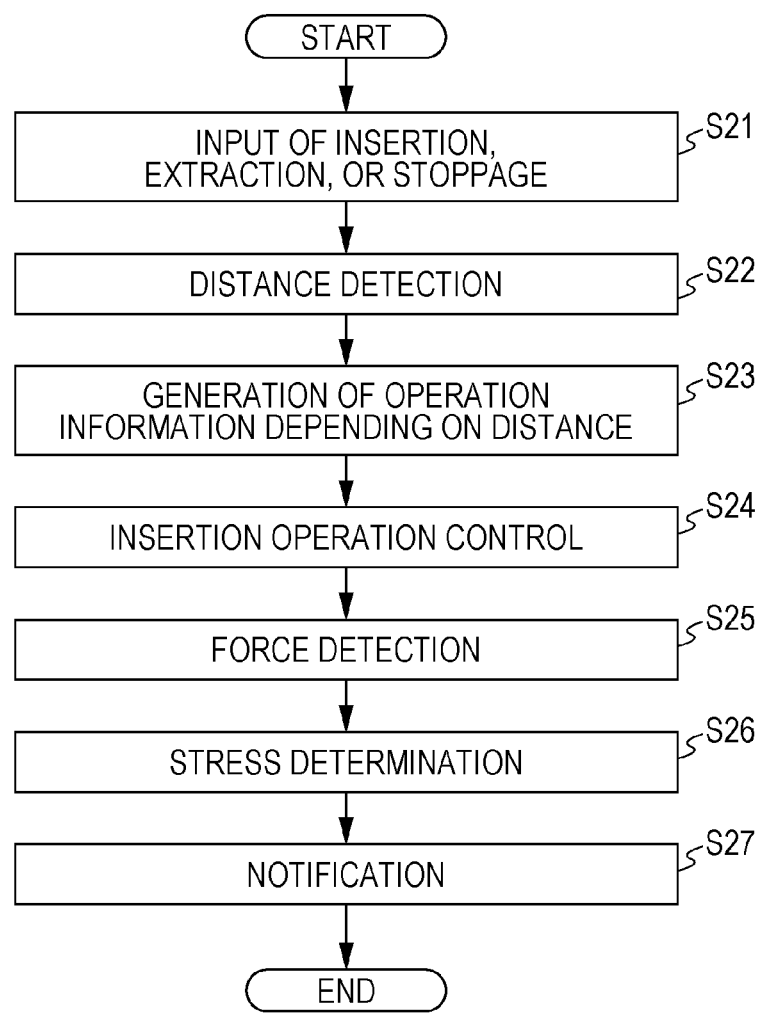
FIG. 23 illustrates a control information database according to the third embodiment of the present disclosure.
FIG. 24 is a flowchart for the insertion apparatus according to the third embodiment of the present disclosure.

FIG. 23 illustrates an example of the contents of the control information stored in the control information database 24.

(1) The Distance Threshold column shows the thresholds used to determine the opened/closed states of the first opening-and-closing portion 12a and the second opening-and-closing portion 12b. The value Le1 corresponds to the first threshold L1 illustrated in FIG. 22A, and the value Le2 corresponds to the second threshold L2 illustrated in FIG. 22A. In the third embodiment, the threshold is expressed in terms of meters.

Timers 16A and 16C

The timer 16A is used to activate the database input/output unit 14 every predetermined period (for example, every 4 msec) and input time information to the operation information database 17 when the operation information is generated.

The timer 16C is used to activate the insertion operation controller 28C every predetermined period (for example, every 4 msec).

Operation Information Generator 9C

The operation information generator 9C generates, as the operation information, the information regarding the opened/closed state of the first opening-and-closing portion 12a and the information regarding the opened/closed state of the second opening-and-closing portion 12b on the basis of the distance L detected by the distance detector 30. The operation information generated by the operation information generator 9C is stored in the operation information database 17 through the database input/output unit 14.

More specifically, first, the insertion operation controller 28C acquires the distance L (illustrated in FIG. 22A) detected by the distance detector 30 from the operation information database 17 through the database input/output unit 14. The insertion operation controller 28C also acquires information regarding the first and second thresholds (L1 and L2) used to determine the opened/closed states of the first opening-and-closing portion 12a and the second opening-and-closing portion 12b from the control information database 24 through the database input/output unit 14.

Figure 22A:
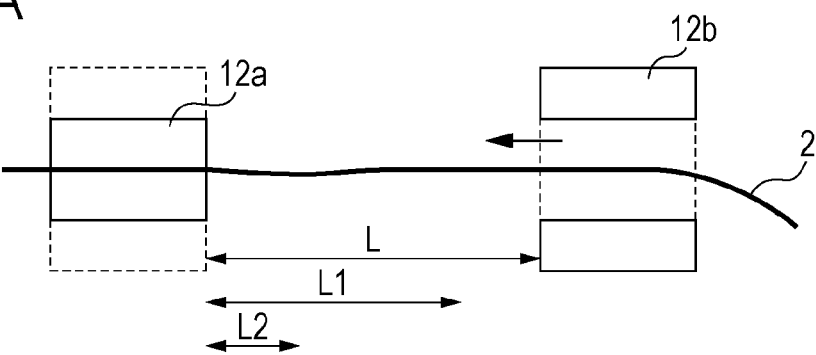
FIG. 22A illustrates the operation of the first opening-and-closing portion and the second opening-and-closing portion according to the third embodiment of the present disclosure.

When the guidewire 2 is to be inserted in the insertion direction, the operator 6 issues a command for insertion in the insertion direction through the input/output IF 7. In this case, in the operation information stored in the operation information database 17, the operation type is set to "1" (movement in the insertion direction). As illustrated in FIG. 22A, the operator 6 holds the second holding unit 19b (second opening-and-closing portion 12b) by hand and moves it in the insertion direction. The insertion operation controller 28C performs the determination operation, which will be described below, on the basis of the command for insertion.

Figure 22B:
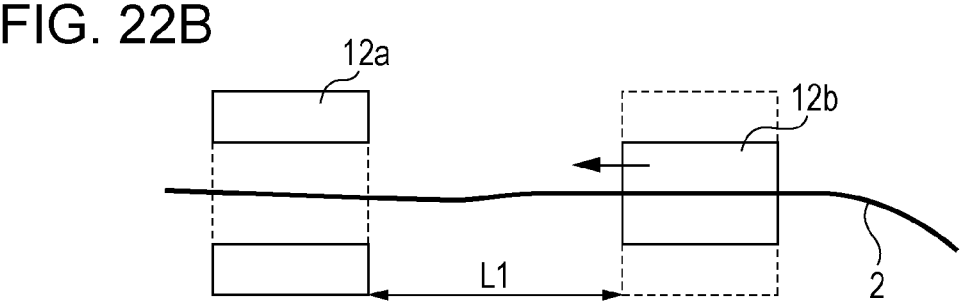
FIG. 22B illustrates the operation of the first opening-and-closing portion and the second opening-and-closing portion according to the third embodiment of the present disclosure.

Next, as illustrated in FIG. 22B, when the insertion operation controller 28C determines that the distance L detected by the distance detector 30 has become greater than or equal to the predetermined first threshold L1, the insertion operation controller 28C controls the operation so that the first opening-and-closing portion 12a is opened and the second opening-and-closing portion 12b is closed. In this case, in the operation information database 17, "0" is stored in the column for the first opening-and-closing portion 12a and "1" is stored in the column for the second opening-and-closing portion 12b as the operation information. In this state, as illustrated in FIG. 22C, the operator 6 holds the second holding unit 19b (second opening-and-closing portion 12b) by hand and moves it in the insertion direction to insert the guidewire 2 further in the insertion direction.

Figure 22C:
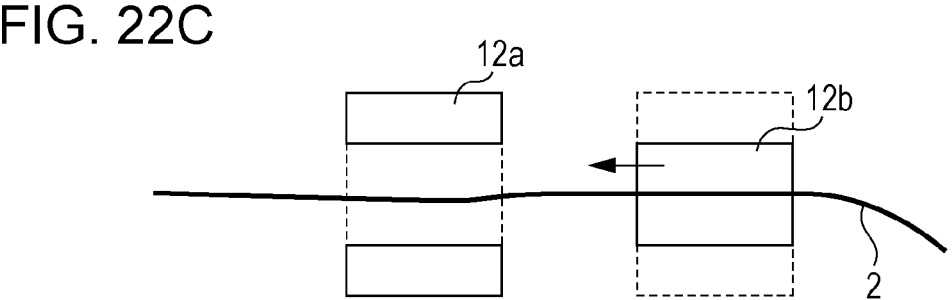
FIG. 22C illustrates the operation of the first opening-and-closing portion and the second opening-and-closing portion according to the third embodiment of the present disclosure.
Figure 22D:
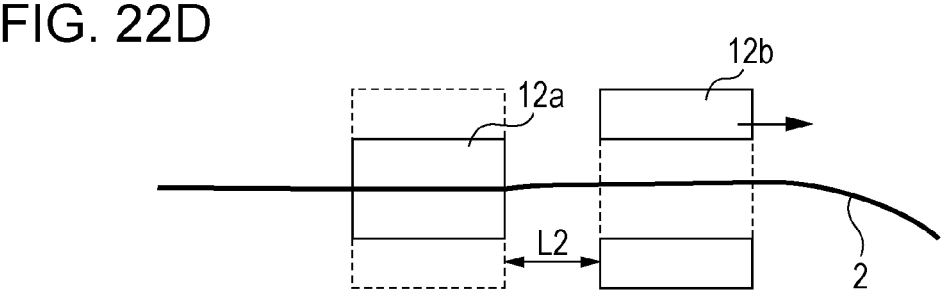
FIG. 22D illustrates the operation of the first opening-and-closing portion and the second opening-and-closing portion according to the third embodiment of the present disclosure.

Next, when the insertion operation controller 28C determines that the distance L detected by the distance detector 30 has become smaller than or equal to the predetermined first threshold L2, the insertion operation controller 28C controls the operation so that the first opening-and-closing portion 12a is closed and the second opening-and-closing portion 12b is opened, as illustrated in FIG. 22D. In this case, in the operation information database 17, "1" is stored in the column for the first opening-and-closing portion 12a and "0" is stored in the column for the second opening-and-closing portion 12b as the operation information. In this state, the operator 6 can move the second opening-and-closing portion 12b backward (in the direction opposite to the insertion direction).

The guidewire 2 can be inserted by repeating the processes illustrated in FIGS. 22A to 22D.

Figure 22E:
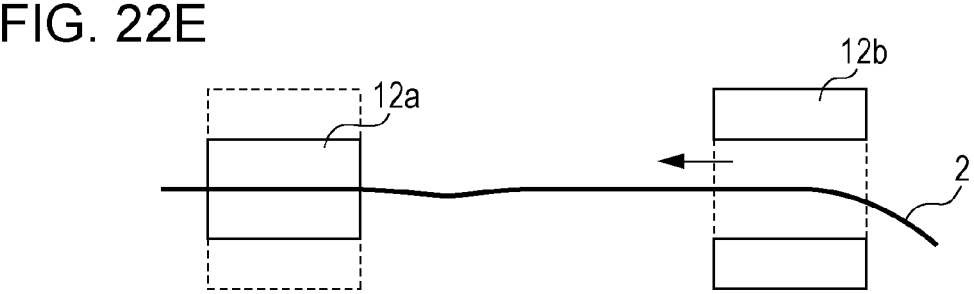
FIG. 22E illustrates the operation of the first opening-and-closing portion and the second opening-and-closing portion according to the third embodiment of the present disclosure.
Figure 22F:
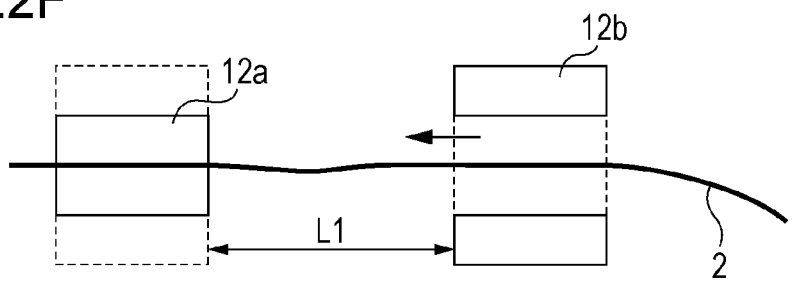
FIG. 22F illustrates the operation of the first opening-and-closing portion and the second opening-and-closing portion according to the third embodiment of the present disclosure.
Figure 22G:
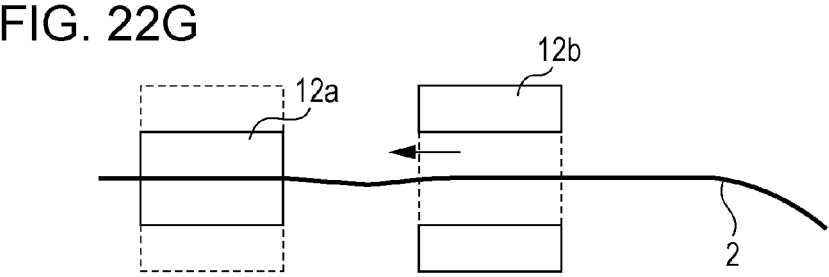
FIG. 22G illustrates the operation of the first opening-and-closing portion and the second opening-and-closing portion according to the third embodiment of the present disclosure.
Figure 22H:
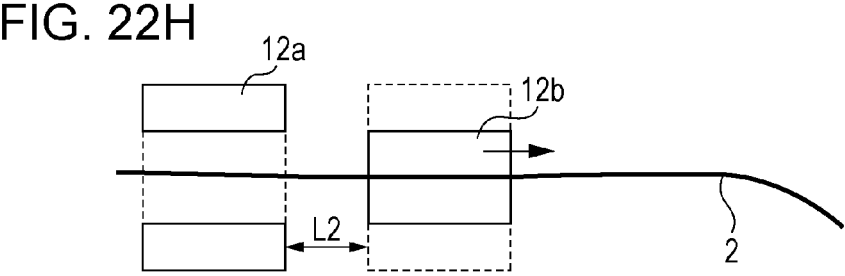
FIG. 22H illustrates the operation of the first opening-and-closing portion and the second opening-and-closing portion according to the third embodiment of the present disclosure.

When the state shown in FIG. 22C is changed to the state shown in FIG. 22D or when the state shown in FIG. 22G is changed to the state shown in FIG. 22H, switching between the first holding unit 19a and the second holding unit 19b occurs. In this case, similar to the first embodiment, there may be a possibility that the force variation over time will fluctuate due to the switching between the first holding unit 19a and the second holding unit 19b. In such a case, for example, the determining unit 26 may determine that no stress is placed on the blood vessel 3 for the force detected in a period from the time when a command to close the first holding unit 19a is issued (time "ts" in the graph of FIG. 9B) to the time after a certain duration of time (time "te" in the graph of FIG. 9B). In addition, similar to the second embodiment, the step in which the first holding unit 19a and the second holding unit 19b are both closed may be performed between the states illustrated in FIGS. 22C and 22D and between the states illustrated in FIGS. 22G and 22H.

When the guidewire 2 is to be moved in the direction opposite to the insertion direction, the operator 6 issues a command for the movement in the direction opposite to the insertion direction through the input/output IF 7. In this case, in the operation information stored in the operation information database 17, the operation type is set to "2" (movement in the direction opposite to the insertion direction). As illustrated in FIG. 22E, the operator 6 holds the second holding unit 19b (second opening-and-closing portion 12b) by hand and moves it in the insertion direction.

Next, as illustrated in FIG. 22F, when the insertion operation controller 28C determines that the distance L detected by the distance detector 30 has become greater than or equal to the predetermined first threshold L1, the insertion operation controller 28C controls the operation so that the first opening-and-closing portion 12a is closed and the second opening-and-closing portion 12b is opened. In this case, in the operation information database 17, "1" is stored in the column for the first opening-and-closing portion 12a and "0" is stored in the column for the second opening-and-closing portion 12b as the operation information. In this state, as illustrated in FIG. 22G, the second holding unit 19b (second opening-and-closing portion 12b) is moved in the insertion direction.

Next, when the insertion operation controller 28C determines that the distance L detected by the distance detector 30 has become smaller than or equal to the predetermined first threshold L2, the insertion operation controller 28C controls the operation so that the first opening-and-closing portion 12a is opened and the second opening-and-closing portion 12b is closed, as illustrated in FIG. 22H. In this case, in the operation information database 17, "0" is stored in the column for the first opening-and-closing portion 12a and "1" is stored in the column for the second opening-and-closing portion 12b as the operation information. In this state, the guidewire 2 can be moved in the direction opposite to the insertion direction.

The guidewire 2 can be moved in the direction opposite to the insertion direction by repeating the processes illustrated in FIGS. 22E to 22H.

When the insertion of the guidewire 2 is to be stopped, the operator 6 issues an insertion stop command through the input/output IF 7. In this case, in the operation information stored in the operation information database 17, the operation type is set to "0".

Figure 22I:
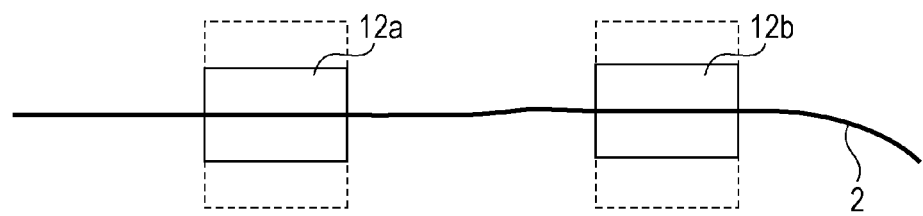
FIG. 22I illustrates the operation of the first opening-and-closing portion and the second opening-and-closing portion according to the third embodiment of the present disclosure.

As illustrated in FIG. 22I, to prevent the guidewire 2 from being moved accidentally, the first opening-and-closing portion 12a and the second opening-and-closing portion 12b are both closed under the control of the insertion operation controller 28C, and "1" is stored in both the column for the first opening-and-closing portion 12a and the column for the second opening-and-closing portion 12b as the operation information in the operation information database 17.

In FIG. 22I, the first opening-and-closing portion 12a and the second opening-and-closing portion 12b are both closed under the control of the insertion operation controller 28C to prevent the guidewire 2 from being moved accidentally. However, the second opening-and-closing portion 12b may be opened.

In the third embodiment, the thresholds L1 and L2 used when the guidewire 2 is inserted are the same as the thresholds L1 and L2 used when the guidewire 2 is extracted. However, thresholds used for insertion may be different from those used for extraction. In such a case, thresholds L1 and L2 for insertion and thresholds L1 and L2 for extraction are stored in the control information database 24.

Insertion Operation Controller 28C

The insertion operation controller 28C controls the opening/closing operation of the first holding unit 19a and the second holding unit 19b on the basis of the operation information generated by the operation information generator 9C.

Force Sensor 13

The force sensor 13 is fixed to one end of the second support portion 11b and includes, for example, a single-axis force sensor. The force sensor 13 detects, through the second opening-and-closing portion 12b, the force generated when the guidewire 2 that has been inserted into the human body 4 from the outside comes into contact with the blood vessel 3. The information detected by the force sensor 13 is stored in the operation information database 17 through the database input/output unit 14, and is input to the determining unit 26.

Determining Unit 26

The determining unit 26 determines whether or not the value of the force detected by the force sensor 13 is greater than or equal to a predetermined threshold (for example, 0.5 N). When the value of the force detected by the force sensor 13 is greater than or equal to the predetermined threshold (for example, 0.5 N), the determining unit 26 determines that stress is placed on the blood vessel 3. The result of the determination is output to the notifying unit 8 together with the force detected by the force sensor 13. When the value of the force detected by the force sensor 13 is less than the predetermined stress detection threshold (for example, 0.5 N), the determining unit 26 determines that no stress is applied to the blood vessel 3. In this case, the result of the determination may or may not be output to the notifying unit 8 together with the force detected by the force sensor 13.

Notifying Unit 8

The notifying unit 8 is a device that notifies the operator of the result of the determination performed by the determining unit 26, and includes, for example, the monitor 8a.

More specifically, as in the monitor 8a illustrated in FIG. 10, the force P [N] detected by the force sensor 13 may be displayed together with the X-ray image. When the determining unit 26 determines that stress is placed on the blood vessel 3, a warning, such as a message "ALERT", may be additionally displayed.

In addition, when the determining unit 26 determines that stress is placed on the blood vessel 3, the speaker 8*b* may emit a warning sound to warn the operator 6.

Next, the operation steps carried out by the insertion apparatus 1 according to the third embodiment will be described. FIG. 24 is a flowchart for the insertion apparatus 1C according to the third embodiment.

A command to start the insertion is received through the input/output IF 7. In Step S21, the insertion apparatus 1C receives an input from the operator 6 through the input/output IF 7, the input indicating whether the guidewire 2 is to be inserted in the insertion direction, moved in the direction opposite to the insertion direction, or stopped.

Next, in Step S22, the distance is intermittently detected by the distance detector 30 (for example, once every predetermined time period), and the information detected by the distance detector 30 is stored in the operation information database 17 through the database input/output unit 14.

Next, in Step S23, the operation information generator 9C generates the operation information for the first opening-and-closing portion 12*a* and the second opening-and-closing portion 12*b* on the basis of the distance stored in the operation information database 17 and the information of the operation type indicating whether the guidewire 2 is to be inserted in the insertion direction, moved in the direction opposite to the insertion direction, or stopped. The generated operation information is stored in the operation information database 17 together with the time.

Next, in Step S24, the insertion operation controller 28C controls the insertion operation by controlling the opened/closed states of the first opening-and-closing portion 12*a* and the second opening-and-closing portion 12*b* on the basis of the operation information stored in the operation information database 17.

Next, in Step S25, the force sensor 13 detects the force applied to the guidewire 2 while the insertion operation mechanism 29C is in operation.

Next, in Step S26, the determining unit 26 determines whether or not stress is placed on the blood vessel 3 on the basis of the detection value obtained by the force sensor 13.

Next, in Step S27, when the determining unit 26 has determined that stress is placed on the blood vessel 3 on the basis of the detection value obtained by the force sensor 13, the result of the determination is presented to the operator 6 through the monitor 8*a* or the speaker 8*b*. When the determining unit 26 has determined that stress is not placed on the blood vessel 3 on the basis of the detection value obtained by the force sensor 13, the result of the determination may or may not be presented to the operator 6 through the monitor 8*a* or the speaker 8*b*.

After that, when a command to end the insertion is issued through the input/output IF 7, the insertion is ended. When no command to end the insertion is issued, Steps S21 to S27 are repeated.

Effects of Third Embodiment

As described above, the robot 19C includes the first holding unit 19*a* and the second holding unit 19*b*. By controlling each of the first holding unit 19*a* and the second holding unit 19*b*, the force applied when a flexible elongate member is inserted can be detected by using a known strain gauge or the like without using a master robot. Thus, the operation of inserting the flexible elongate member can be assisted by using a robot or the like.

Modifications

In the first and second embodiments, the master movement amount of the master mechanism 23 is set as the amount of movement of the movable portion 19*ca* of the slave mechanism 29. However, the slave mechanism 29 may be controlled so as to reduce or increase the movement of the master mechanism 23. In such a case, the slave mechanism 29 is controlled on the basis of a value obtained by multiplying the amount of movement by a movement gain.

In addition, in the first to third embodiments, when the determining unit 26 determines that stress is placed on the blood vessel 3 or the optical fiber 2B, the operation information generator 9 or 9C may generate the operation information such that the operation of the slave controller 28 or the insertion operation controller 28C is stopped, so that the insertion operation is stopped.

In addition, in the second embodiment, the force transmitting unit 20 transmits the force information detected by the force sensor 13 of the slave robot 19 to the operator 6. However, the transmitted force may be increased so that the force can be more easily recognized, or reduced so that the master mechanism 23 can be supported by a smaller force. Thus, the force information to be transmitted may be multiplied by a force gain.

In addition, in the first and second embodiments, the master mechanism 23 includes the lever 15. However, the speed and direction may instead be set by, for example, a slider or a button.

In addition, in the first and second embodiments, the operation information generator 9 is included in the master robot 18. However, the operation information generator 9 may instead be included in the slave robot 19.

When the guidewire 2 or the optical fiber 2B, which are examples of flexible elongate members, is pulled out from the blood vessel 3 or the fiber tube 3B, respectively, it may be assumed that no stress will be placed on the guidewire 2 or the optical fiber 2B, which are examples of flexible elongate members, or on the blood vessel 3 or the fiber tube 3B. In such a case, the worker or the operator 6 may directly hold the guidewire 2 or the optical fiber 2B, which are examples of flexible elongate members, and pull out the guidewire 2 or the optical fiber 2B from the blood vessel 3 or the fiber tube 3B, respectively while the first opening-and-closing portion 12*a* and the second opening-and-closing portion 12*b* are both opened.

Although the above-described structure is such that the first holding unit 19*a* is fixed and the second holding unit 19*b* is movable, the structure may instead be such that the second holding unit 19*b* is fixed and the first holding unit 19*a* is movable.

Although the first to third embodiments of the present disclosure and modifications thereof have been described, it goes without saying that the present disclosure is not limited to the above-described first to third embodiments and modifications thereof. The present disclosure also includes the following cases.

Specifically, part of each of the above-described insertion apparatuses is a computer system that includes, for example, a microprocessor, a ROM, a RAM, a hard disk unit, a display unit, a keyboard, and a mouse. A computer program is stored on the RAM or the hard disk unit. The microprocessor operates in accordance with the computer program so that each component achieves the function thereof. To achieve predetermined functions, the computer program includes a combination of a plurality of instruction codes that indicate commands for the computer.

For example, each element may be realized by causing a program executing unit, such as a CPU, to read and execute a software program stored in a storage medium, such as a hard disk or a semiconductor memory. Software that realizes one or more of the elements of the insertion apparatuses according to the above-mentioned embodiments and modifications includes the following program. That is, the program is an insertion operation control program for inserting a flexible elongate member into a tube while holding and releasing the flexible elongate member by causing each of a first holding unit and a second holding unit of an insertion apparatus for a flexible elongate member to perform an opening/closing operation. The insertion operation control program includes the steps of acquiring, with an information acquiring unit, information of a distance by which the second holding unit moves with respect to the first holding unit and information of an operation type, and storing the acquired information in a computer, the information of the operation type being used to distinguish between insertion of the flexible elongate member into the tube, stoppage of the flexible elongate member, and extraction of the flexible elongate member from the tube; generating, with an operation information generator, operation information regarding each of an opened/closed state of the first holding portion and an opened/closed state of the second holding portion on the basis of the distance and the operation type acquired by the information acquiring unit; and controlling, with an insertion operation controller, the insertion of the flexible elongate member into the tube, the stoppage of the flexible elongate member, or the extraction of the flexible elongate member from the tube on the basis of the operation information generated by the operation information generator.

The program to be executed may be downloaded from a server or the like or read from a predetermined storage medium (an optical disc such as a CD-ROM, a magnetic disc, or a semiconductor memory).

Furthermore, the program may be executed by one or more computers. Namely, the program may be executed either through centralized processing or distributed processing.

The effects of the above-described embodiments and modifications may be achieved in combination by appropriately combining one or more of the embodiments and modifications.

With the insertion apparatus for a flexible elongate member, the insertion method for a flexible elongate member, and the insertion operation control program according to the present disclosure, the operation of holding units that hold the flexible elongate member is controlled so that the flexible elongate member can be inserted while force measurement is performed by a known train gauge or the like. Thus, the present disclosure is suitable for an operation of inserting a flexible elongate member into a tube by using a robot. Examples of the operation of inserting a flexible elongate member into a tube by using a robot include an operation of inserting a flexible elongate member like a guidewire or a catheter into a tube of a human body, such as a blood vessel, an operation of assembling a flexible elongate member like an optical fiber in a manufacturing or assembling site, and an operation of inserting a flexible elongate member like a wire or a hose through a pipe.

What is claimed is:

1. An apparatus for a flexible elongate member, comprising:
   a first holding unit that is capable of holding the flexible elongate member by closing a first opening-and-closing portion and that is capable of releasing the flexible elongate member by opening the first opening-and-closing portion;
   a second holding unit that is capable of moving with respect to the first holding unit, that performs an opening-and-closing operation independently of an opening-and-closing operation of the first holding unit, that is capable of holding the flexible elongate member by closing a second opening-and-closing portion, and that is capable of releasing the flexible elongate member by opening the second opening-and-closing portion;
   an information acquiring unit that acquires information of a distance of the second holding unit with respect to the first holding unit and information of an operation type including information indicating insertion of the flexible elongate member into a tube, extraction of the flexible elongate member from the tube, or stoppage of the insertion and the extraction;
   an operation information generator that generates operation information on the basis of the acquired information of the distance and the acquired information of the operation type, the operation information including information indicating whether to open or close the first holding unit and information indicating whether to open or close the second holding unit; and
   an operation controller that controls the insertion, the extraction, and the stoppage of the insertion and the extraction on the basis of the operation information.

2. The apparatus according to claim 1, wherein, when the insertion or the extraction is performed, the operation information generator generates, as the operation information, information including information indicating that the first holding unit is to be opened and the second holding unit is to be closed.

3. The apparatus according to claim 1, wherein, when the insertion or the extraction is performed and when the second holding unit is moved while the flexible elongate member is held by the first holding unit, the operation information generator generates, as the operation information, information including information indicating that the first holding unit is to be closed and the second holding unit is to be opened.

4. The apparatus according to claim 2, wherein, when the insertion and the extraction are to be stopped, the operation information generator generates, as the operation information, information including information indicating that the first holding unit is to be closed.

5. The apparatus according to claim 1, wherein, when the insertion or the extraction is performed, the operation information generator generates, as the operation information, information including information indicating that the first holding unit is to be opened and the second holding unit is to be closed after the first holding unit and the second holding unit are closed at the same time.

6. The apparatus according to claim 1, further comprising:
   a master mechanism that acquires the distance as an amount of movement of the flexible elongate member; and
   an insertion unit that moves the second holding unit linearly by a distance corresponding to the amount of movement by a driving operation of a drive device,
   wherein the information of the distance is based on a position of the second holding unit at the insertion unit.

7. The apparatus according to claim 1,
   wherein the information acquiring unit includes a distance detector that detects the distance, wherein, when the operation type is the insertion, the operation information generator generates, as the operation information, information including information indicating that the first holding unit is to be opened and the second holding unit is to be closed at the time when the distance detected by the distance detector becomes greater than or equal to a predetermined first threshold, and then the first holding unit is to be closed and the second holding unit is to be opened to release the flexible elongate member at the time when the distance detected by the distance detector becomes smaller than or equal to a predetermined second threshold, wherein, when the operation type is the extraction, the operation information generator generates, as the operation information, information including information indicating that the first holding unit is to be closed and the second holding unit is to be opened at the time when the distance detected by the distance detector becomes greater than or equal to the predetermined first threshold, and then the first holding unit is to be opened and the second holding unit is to be closed at the time when the distance detected by the distance detector becomes smaller than or equal to the predetermined second threshold, and wherein, when the operation type is the stoppage of the insertion and the extraction, the operation information generator generates, as the operation information, information including information indicating that the first holding unit is to be closed.

8. The apparatus according to claim 1, further comprising:
a force detector that is provided on the second holding unit and that detects information of a force applied to the flexible elongate member; and
a determining unit that determines that stress is placed on the flexible elongate member or the tube when the information of the force detected by the force detector is greater than or equal to a threshold.

9. The apparatus according to claim 8, further comprising:
a first notifying unit that displays a result of the determination performed by the determining unit together with a captured image of the tube or the flexible elongate member.

10. The apparatus according to claim 8, further comprising:
a second notifying unit that emits a sound to notify a worker of a result of the determination performed by the determining unit.

11. The apparatus according to claim 8, wherein, when the determining unit determines that stress is placed on the tube or the flexible elongate member, the operation information generator generates, as the operation information, information indicating that the first holding unit is to be closed.

12. The apparatus according to claim 8, further comprising:
a force transmitting unit that transmits a force to a master mechanism on the basis of the force detected by the force detector, the master mechanism being manipulated by a worker.

13. A method for a flexible elongate member, comprising:
acquiring information of a distance of a second holding unit with respect to a first holding unit and information of an operation type including information indicating insertion of the flexible elongate member into a tube, extraction of the flexible elongate member from the tube, or stoppage of the insertion and the extraction, the first holding unit being capable of holding the flexible elongate member by closing a first opening-and-closing portion and being capable of releasing the flexible elongate member by opening the first opening-and-closing portion, the second holding unit being capable of moving with respect to the first holding unit, performing an opening-and-closing operation independently of an opening-and-closing operation of the first holding unit, being capable of holding the flexible elongate member by closing a second opening-and-closing portion, and being capable of releasing the flexible elongate member by opening the second opening-and-closing portion;
generating operation information on the basis of the acquired information of the distance and the acquired information of the operation type, the operation information including information indicating whether to open or close the first holding unit and information indicating whether to open or close the second holding unit; and
controlling the insertion, the extraction, and the stoppage of the insertion and the extraction on the basis of the operation information.

14. A non-transitory computer-readable storage medium that stores a control program for causing an apparatus including a processor to execute a method for a flexible elongate member, the method comprising:
acquiring information of a distance of a second holding unit with respect to a first holding unit and information of an operation type including information indicating insertion of the flexible elongate member into a tube, extraction of the flexible elongate member from the tube, or stoppage of the insertion and the extraction, the first holding unit being capable of holding the flexible elongate member by closing a first opening-and-closing portion and being capable of releasing the flexible elongate member by opening the first opening-and-closing portion, the second holding unit being capable of moving with respect to the first holding unit, performing an opening-and-closing operation independently of an opening-and-closing operation of the first holding unit, being capable of holding the flexible elongate member by closing a second opening-and-closing portion, and being capable of releasing the flexible elongate member by opening the second opening-and-closing portion;
generating operation information on the basis of the acquired information of the distance and the acquired information of the operation type, the operation information including information indicating whether to open or close the first holding unit and information indicating whether to open or close the second holding unit; and
controlling the insertion, the extraction, and the stoppage of the insertion and the extraction on the basis of the operation information.

* * * * *